(12) United States Patent
Tsukamoto et al.

(10) Patent No.: US 6,770,597 B2
(45) Date of Patent: Aug. 3, 2004

(54) BENZOHYDRAZIDE DERIVATIVES AS HERBICIDES AND DESICCANT COMPOSITIONS CONTAINING THEM

(75) Inventors: Masamitsu Tsukamoto, Moriyama (JP); Mark Read, Willoughby, OH (US)

(73) Assignee: Ishihara Sangyo Kaisha, Ltd., Osaka (JP)

( * ) Notice: Subject to any disclaimer, the term of this patent is extended or adjusted under 35 U.S.C. 154(b) by 0 days.

(21) Appl. No.: 10/196,220

(22) Filed: Jul. 17, 2002

(65) Prior Publication Data

US 2004/0018942 A1 Jan. 29, 2004

(51) Int. Cl.⁷ .................. C07D 231/12; C07D 231/14; C07D 239/54; A01N 43/26; A01N 43/32
(52) U.S. Cl. .................. 504/243; 504/280; 544/311; 544/312; 548/370.1; 548/375.1
(58) Field of Search .................. 544/311, 312; 548/370.1, 375.1; 504/243, 280

(56) References Cited

U.S. PATENT DOCUMENTS 5,281,571 A * 1/1994 Woodard et al. ............ 504/225
5,466,663 A * 11/1995 Hiratsuka et al. ........... 504/286

OTHER PUBLICATIONS

Chem. Abstract vol. 114, No. 5, Feb. 4, 1991 (Columbus, OH, USA), p. 692, column 2, the abstract No. 42219f, Koul, S.K. 'Synthesis of antiubercular compounds based in the isoniazid model.' Indian Drugs 1990, 27(4), 227–38 (Eng).

* cited by examiner

Primary Examiner—Deepak Rao
(74) Attorney, Agent, or Firm—Sughrue Mion, PLLC

(57) ABSTRACT

The compound of the formula:

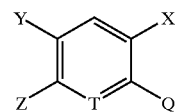

wherein Y, X, Z, T and Q are defined in the specification,

15 Claims, No Drawings

BENZOHYDRAZIDE DERIVATIVES AS HERBICIDES AND DESICCANT COMPOSITIONS CONTAINING THEM

BACKGROUND OF THE INVENTION

1. Field of the Invention

The present invention relates to novel benzohydrazide derivatives, their salts and compositions containing them, intermediates, a process for producing them, and their use as herbicides.

2. Description of the Related Art

EP 195346 disclosed the herbicidal utility of uracil derivatives, in which the phenyl ring of the described compounds were substituted by carboxyl moiety. JP 01139581 and WO 92/06962 disclosed benzohydrazide, in which the phenyl ring of the described compounds were substituted by tetrahydrophthalamide and pyrazole moiety respectively. WO99/52878 described benzohydrazide derivatives with pyridazinone moiety. EP0745599 described thiotrione derivatives as an intermediate. WO97/33875 and WO97/40018 disclosed benzonitrile derivatives. Phthalimide derivative was disclosed in Indian J. Chem., Sect. B (1986), 25B(3), 308–311. Despite the broad coverage of these patents and literature, the general structure of the present invention has not been described.

The specific benzohydrazides and related compounds of the formula I mentioned below are novel and can be used to effectively control a variety of broad or grassy leaf plant species.

SUMMARY OF THE INVENTION

The invention delineates a method for the control of undesired vegetation in a plantation crop by the application to the locus of the crop an effective amount of a compound described herein. The present application describes certain herbicidal benzohydrazide derivatives of the formula (I) including all geometric, tautomeric and stereoisomers, and their salts, as well as compositions containing them and methods of preparation for these compounds.

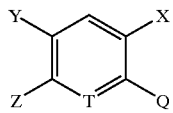

I wherein

X is hydrogen or halogen;

Y is represented by hydrogen, halogen, nitro, $(C_{1-4})$alkyl, $(C_{1-4})$alkoxy, $(C_{1-4})$haloalkyl or $(C_{1-4})$haloalkoxy;

T is represented by N or CH;

Z is one of the following groups;

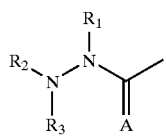

II

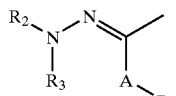

III

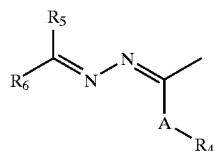

IV

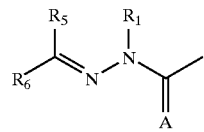

V

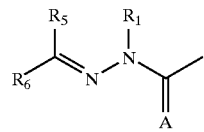

VI

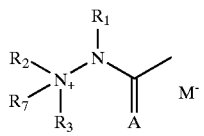

VII

A is oxygen, sulfur or $NR_4$;

$R_1$, $R_2$, $R_3$ and $R_4$ are independent of each other and may be selected from the group consisting of hydrogen, cyano, $(C_{1-6})$alkyl, $(C_{1-6})$haloalkyl, $(C_{1-6})$alkoxy,$(C_{1-6})$haloalkoxy, $(C_{1-6})$alkoxyalkyl, $(C_{2-6})$alkynyl, $(C_{2-6})$alkenyl, aryl, heteroaryl, aryloxy, heteroaryloxy, $(C_{3-6})$cycloalkyl, $(C_{3-6})$cyclocarbonyl, carboxy, $(C_{1-6})$alkylcarbonyl, arylcarbonyl, $(C_{1-3})$haloalkylcarbonyl, $(C_{1-6})$alkylcarbonyloxy, $(C_{1-6})$haloalkylcarbonyloxy, $(C_{1-6})$alkoxycarbonyl, $(C_{1-6})$haloalkoxycarbonyl, $(C_{1-6})$alkylthiocarbonyl, $(C_{1-6})$haloalkylthiocarbonyl, $(C_{1-6})$alkoxythiocarbonyl, $(C_{1-6})$haloalkoxythiocarbonyl,$(C_{1-6})$alkylamino, arylsulfonylamino, arylamino, $(C_{1-6})$alkylthio, arylthio, $(C_{2-6})$alkenylthio, $(C_{2-6})$alkynylthio, $(C_{1-6})$alkylsulfinyl, $(C_{2-6})$alkenylsulfinyl, $(C_{2-6})$alkynylsulfinyl, $(C_{1-6})$alkylsulfonyl, $(C_{2-6})$alkenylsulfonyl, $(C_{2-6})$alkynylsulfonyl, arylsulfonyl, where any of these groups may be optionally substituted with one or one more of the following group consisting of halogen, hydroxy, mercapto, cyano, nitro, amino, caboxy, $(C_{1-6})$alkyl, $(C_{1-6})$haloalkyl, $(C_{1-6})$alkylcarbonyl, $(C_{1-6})$alkylcarbonyloxy, $(C_{1-6})$haloalkylcarbonyl, $(C_{1-6})$haloalkylcarbonyloxy, $(C_{1-6})$alkoxy, $(C_{1-6})$alkoxycarbonyl, aminocarbonyl, $(C_{1-6})$alkylaminocarbonyl, $(C_{1-6})$haloalkoxy, $(C_{1-6})$haloalkoxycarbonyl, $(C_{1-6})$alkylsulfonyl, $(C_{1-6})$haloalkylsulfonyl, aryl, haloaryl, alkoxyaryl, aryoxy, arylthio, haloaryloxy, heteroaryl, heteroaryloxy and $(C_{3-7})$cycloalkyl;

When $R_2$ and $R_3$ are taken together with the atoms to which they are attached, they represent a three to seven membered substituted or unsubstituted ring optionally containing oxygen, carbonyl, $S(O)_{n^{**}}$ or nitrogen with following optional substitutions, one to three halogen, cyano, nitro, hydroxy, amino, carbonyl, $(C_{1-6})$alkyl, $(C_{1-6})$haloalkyl, $(C_{1-6})$alkylcarbonyl, $(C_{1-6})$alkylcarbonyloxy, $(C_{1-6})$haloalkylcarbonyl, $(C_{1-6})$ haloalkylcarbonyloxy, ($C_{1-6}$)alkoxy, ($C_{1-6}$)alkoxycarbonyl, aminocarbonyl, ($C_{1-6}$)alkylaminocarbonyl, ($C_{1-6}$)haloalkoxy, ($C_{1-6}$)haloalkoxycarbonyl, ($C_{1-6}$)alkylsulfonyl, ($C_{1-6}$)haloalkylsulfonyl, aryl, heteroaryl or ($C_{3-7}$)cycloalkyl;

$R_5$ and $R_6$ are independent of each other and may be selected from the group consisting of hydrogen, ($C_{1-6}$)alkyl, ($C_{2-6}$)alkenyl, ($C_{2-6}$)alkynyl, ($C_{1-6}$)alkoxycarbonyl and heteroarylcarbonyl;

where any of these groups may be optionally substituted with one or more of the following groups consisting of halogen, hydroxy, cyano, nitro, amino, caboxyl, ($C_{1-6}$)alkyl, ($C_{1-6}$)haloalkyl, ($C_{1-6}$)alkylcarbonyl, ($C_{1-6}$)alkylcarbonyloxy, ($C_{1-6}$)haloalkylcarbonyl, ($C_{1-6}$)haloalkylcarbonyloxy, ($C_{1-6}$)alkoxy, ($C_{1-6}$)alkoxycarbonyl, aminocarbonyl, ($C_{1-6}$)alkylaminocarbonyl, ($C_{1-6}$)haloalkoxy, ($C_{1-6}$)haloalkoxycarbonyl, ($C_{1-6}$)alkylsulfonyl, ($C_{1-6}$)haloalkylsulfonyl, aryl, heteroaryl and ($C_{3-7}$)cycloalkyl;

When $R_5$ and $R_6$ are taken together with the atoms to which they are attached, they represent a three to seven membered substituted or unsubstituted ring optionally containing oxygen, carbonyl, $S(O)_{n^{**}}$ or nitrogen with following optional substitutions, one to three halogen, cyano, nitro, hydroxy, amino, carbonyl, ($C_{1-6}$)alkyl, ($C_{1-6}$)haloalkyl, ($C_{1-6}$)alkylcarbonyl, ($C_{1-6}$)alkylcarbonyloxy, ($C_{1-6}$)haloalkylcarbonyl, ($C_{1-6}$)haloalkylcarbonyloxy, ($C_{1-6}$)alkoxy, ($C_{1-6}$)alkoxycarbonyl, aminocarbonyl, ($C_{1-6}$)alkylaminocarbonyl, ($C_{1-6}$)haloalkoxy, ($C_{1-6}$)haloalkoxycarbonyl, ($C_{1-6}$)alkylsulfonyl, ($C_{1-6}$)haloalkylsulfonyl, aryl, heteroaryl or ($C_{3-7}$)cycloalkyl;

$R_7$ may be selected from the group consisting of hydrogen, ($C_{1-6}$)alkyl, ($C_{2-6}$)alkenyl or ($C_{2-6}$)alkynyl where any of these groups may be optionally substituted with one or more of the following groups consisting of halogen, hydroxy, cyano, nitro, amino, caboxyl, ($C_{1-6}$)alkyl, ($C_{1-6}$)haloalkyl, ($C_{1-6}$)alkylcarbonyl, ($C_{1-6}$)alkylcarbonyloxy, ($C_{1-6}$)haloalkylcarbonyl, ($C_{1-6}$)haloalkylcarbonyloxy, ($C_{1-6}$)alkoxy, ($C_{1-6}$)alkoxycarbonyl, aminocarbonyl, ($C_{1-6}$)alkylaminocarbonyl, ($C_{1-6}$)haloalkoxy, ($C_{1-6}$)haloalkoxycarbonyl, ($C_{1-6}$)alkylsulfonyl, ($C_{1-6}$)haloalkylsulfonyl, aryl, heteroaryl and ($C_{3-7}$)cycloalkyl;

M is halogen, dichloroiodate, tetrachloroiodate, sulfate, nitrate, formate, acetate, propionate or butylate.

Q is selected from;

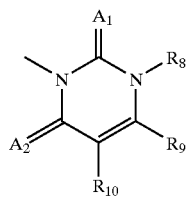

Q₁

-continued

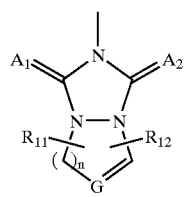

Q₂

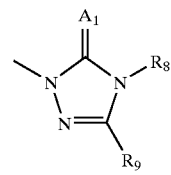

Q₃

Q₄

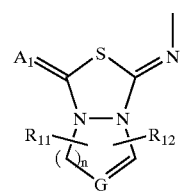

Q₅

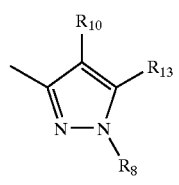

Q₆

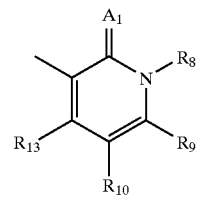

Q₇

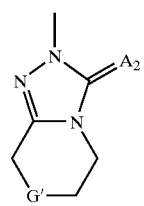

Q₈

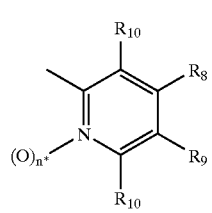

Q₉

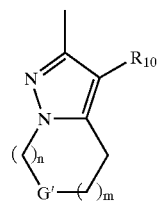

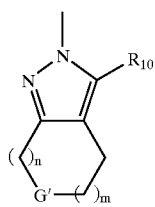

Q10

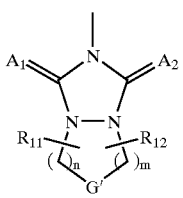

Q11

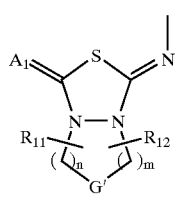

Q12 wherein
- $A_1$ and $A_2$ are independently oxygen or sulfur;
- $R_8$ is hydrogen, halogen, cyano, nitro, formyl $(C_{1-4})$alkyl, $(C_{1-4})$haloalkyl, amino, $(C_{1-4})$alkylamino, $(C_{1-4})$haloalkylamino, $(C_{1-4})$alyloxyamino, $(C_{1-4})$haloalkoxyamino, $(C_{1-4})$alkylcarbonyl, $(C_{1-4})$haloalkylcarbonyl, $(C_{1-4})$haloalkoxycarbonyl, $(C_{1-4})$alkylcabonylamino, $(C_{1-4})$haloalkylcarbonylamino, $(C_{1-4})$alkoxycarbonylamino, $(C_{1-4})$haloalkoxycarbonylamino, $(C_{1-6})$alkoxyalkyl, $(C_{1-6})$haloalkoxyalkyl, $(C_{1-6})$alkylthio, $(C_{1-6})$haloalkylthio, $(C_{2-6})$alkenyl, $(C_{2-6})$haloalkenyl, $(C_{2-6})$alkynyl or $(C_{2-6})$haloalkynyl;
- $R_9$ and $R_{10}$ are independent of each other and may be selected from the group consisting of hydrogen, halogen, cyano, $(C_{1-4})$alkyl, $(C_{1-4})$haloalkyl, $(C_{1-4})$alkoxy, $(C_{1-4})$haloalkoxy, $(C_{2-6})$alkenyl, $(C_{2-6})$haloalkenyl.
- $R_{11}$ and $R_{12}$ are independent of each other and may be selected from the group consisting of hydrogen, halogen, $(C_{1-3})$alkyl, $(C_{1-3})$haloalkyl, hydroxy, $(C_{1-3})$alkoxy, $(C_{1-3})$haloalkoxy, cyano, nitro, amino or $(C_{1-6})$alkylamino;
- When $R_{11}$ and $R_{12}$ are taken together with the atoms to which they are attached, they represent a three to seven membered substituted or unsubstituted ring optionally containing oxygen, $S(O)_{n^{**}}$ or nitrogen with following optional substitutions, one to three halogen, cyano, nitro, hydroxy, amino, carbonyl, $(C_{1-6})$alkyl, $(C_{1-6})$haloalkyl, $(C_{1-6})$alkylcarbonyl, $(C_{1-6})$alkylcarbonyloxy, $(C_{1-6})$haloalkylcarbonyl, $(C_{1-6})$haloalkylcarbonyloxy, $(C_{1-6})$alkoxy, $(C_{1-6})$alkoxycarbonyl, aminocarbonyl, $(C_{1-6})$alkylaminocarbonyl, $(C_{1-6})$haloalkoxy, $(C_{1-6})$haloalkoxycarbonyl, $(C_{1-6})$alkylsulfonyl, $(C_{1-6})$haloalkylsulfonyl, aryl, heteroaryl or $(C_{3-7})$cycloalkyl;
- $R_{13}$ may be selected from the group consisting of hydrogen, halogen, cyano, $(C_{1-4})$alkyl, $(C_{1-4})$alkoxy, $(C_{1-4})$haloalkoxy, $(C_{1-4})$alkylthio, $(C_{1-4})$haloalkylthio, $(C_{1-4})$alkylsulfinyl, $(C_{1-4})$haloalkylsulfinyl, $(C_{1-4})$alkylsulfonyl, $(C_{1-4})$haloalkylsulfonyl $(C_{2-6})$alkenyl or $(C_{2-6})$haloalkenyl.
- G is nitrogen or $CR_{15}$;
- G' is carbonyl, $NR_{14}$, oxygen, $S(O)_{n^{**}}$ or $CR_{15}R_{16}$;
- $R_{14}$ may be selected from the group consisting of hydrogen, $(C_{1-6})$alkyl, $(C_{1-6})$alkylcarbonyl, $(C_{1-6})$haloalkylcarbonyl, arylcarbonyl and heteroarylcarbonyl; where any of these groups may be optionally substituted with one or more of the following groups consisting of halogen, hydroxy, cyano, nitro, amino, caboxyl, $(C_{1-6})$alkyl, $(C_{1-6})$haloalkyl, $(C_{1-6})$alkylcarbonyl, $(C_{1-6})$alkylcarbonyloxy, $(C_{1-6})$haloalkylcarbonyl, $(C_{1-6})$haloalkylcarbonyloxy, $(C_{1-6})$alkoxy, $(C_{1-6})$alkoxycarbonyl, aminocarbonyl, $(C_{1-6})$alkylaminocarbonyl, $(C_{1-6})$haloalkoxy, $(C_{1-6})$haloalkoxycarbonyl, $(C_{1-6})$alkylsulfonyl, $(C_{1-6})$haloalkylsulfonyl, aryl, heteroaryl and $(C_{3-7})$cycloalkyl;
- $R_{15}$ and $R_{16}$ are independent of each other and may be selected from the group consisting of hydrogen, halogen, hydroxy, mercapto, amino, cyano, $(C_{1-6})$alkyl, $(C_{1-6})$haloalkyl, $(C_{1-6})$alkoxy,$(C_{1-6})$haloalkoxy, $(C_{1-6})$alkoxyalkyl, $(C_{2-6})$alkynyl, $(C_{2-6})$alkenyl, aryl, heteroaryl, aryloxy, heteroaryloxy, $(C_{3-6})$cycloalkyl, $(C_{3-6})$cyclocarbonyl, carboxy, $(C_{1-6})$alkylcarbonyl, arylcarbonyl, $(C_{1-3})$haloalkylcarbonyl, $(C_{1-6})$alkylcarbonyloxy, $(C_{1-6})$haloalkylcarbonyloxy, $(C_{1-6})$alkoxycarbonyl, $(C_{1-6})$haloalkoxycarbonyl, $(C_{1-6})$alkylthiocarbonyl, $(C_{1-6})$haloalkylthiocarbonyl, $(C_{1-6})$alkoxythiocarbonyl, $(C_{1-6})$haloalkoxythiocarbonyl,$(C_{1-6})$alkylamino, arylsulfonylamino, arylamino, $(C_{1-3})$alkylthio, arylthio, $(C_{2-6})$alkenylthio, $(C_{2-6})$alkynylthio, $(C_{1-6})$alkylsulfinyl, $(C_{2-6})$alkenylsulfinyl, $(C_{2-6})$alkynylsulfinyl, $(C_{1-6})$alkylsulfonyl, $(C_{2-6})$alkenylsulfonyl, $(C_{2-6})$alkynylsulfonyl, arylsulfonyl, where any of these groups may be optionally substituted with one or one more of the following group consisting of halogen, hydroxy, mercapto, cyano, nitro, amino, caboxyl, $(C_{1-6})$alkyl, $(C_{1-6})$haloalkyl, $(C_{1-6})$alkylcarbonyl, $(C_{1-6})$alkylcarbonyloxy, $(C_{1-6})$haloalkylcarbonyl, $(C_{1-6})$haloalkylcarbonyloxy, $(C_{1-6})$alkoxy, $(C_{1-6})$alkoxycarbonyl, aminocarbonyl, $(C_{1-6})$alkylaminocarbonyl, $(C_{1-6})$haloalkoxy, $(C_{1-6})$haloalkoxycarbonyl, $(C_{1-6})$alkylsulfonyl, $(C_{1-6})$haloalkylsulfonyl, aryl, heteroaryl and $(C_{3-7})$cycloalkyl;
- n and m are independent of each other and represent an integer from 0 to 2; provided that m+n is 2, 3 or 4;
- $n^*$ is 0 or 1;
- $n^{**}$ is represent an integer from 0 to 2;

Preferred formula (I) compounds of this invention are those wherein
- X is hydrogen or halogen;
- Y is represented by hydrogen, halogen, nitro, $(C_{1-4})$haloalkyl or $(C_{1-4})$haloalkoxy;
- T is CH;
- Z is selected from group (II), (III) or (V);
- A is oxygen or sulfur;
- $R_1$, $R_2$, $R_3$ and $R_4$ are independent of each other and may be selected from the group consisting of hydrogen, $(C_{1-6})$alkyl, $(C_{1-6})$haloalkyl, $(C_{1-6})$alkoxy,$(C_{1-6})$haloalkoxy, $(C_{1-6})$alkoxyalkyl, $(C_{2-6})$alkynyl, $(C_{2-6})$alkenyl, aryl, heteroaryl, aryloxy, heteroaryloxy, $(C_{3-6})$cycloalkyl, $(C_{3-6})$cyclocarbonyl, carboxy, $(C_{1-6})$alkylcarbonyl, arylcarbonyl, $(C_{1-3})$, $(C_{1-6})$ alkoxycarbonyl, $(C_{1-6})$haloalkoxycarbonyl, $(C_{1-6})$alkylthiocarbonyl, $(C_{1-6})$alkoxythiocarbonyl, $(C_{1-6})$alkylamino, arylsulfonylamino, arylamino, $(C_{1-6})$alkylthio, arylthio, $(C_{2-6})$alkenylthio, $(C_{1-6})$alkylsulfinyl, $(C_{2-6})$alkenylsulfinyl, $(C_{2-6})$alkynylsulfinyl, $(C_{1-6})$alkylsulfonyl, $(C_{2-6})$alkenylsulfonyl, arylsulfonyl, where any of these groups may be optionally substituted with one or one more of the following group consisting of halogen, hydroxy, mercapto, cyano, nitro, amino, caboxy, $(C_{1-6})$alkyl, $(C_{1-6})$haloalkyl, $(C_{1-6})$alkylcarbonyl, $(C_{1-6})$alkylcarbonyloxy, $(C_{1-6})$haloalkylcarbonyl, $(C_{1-6})$haloalkylcarbonyloxy, $(C_{1-6})$alkoxy, $(C_{1-6})$alkoxycarbonyl, aminocarbonyl, $(C_{1-6})$alkylaminocarbonyl, $(C_{1-6})$haloalkoxy, $(C_{1-6})$haloalkoxycarbonyl, $(C_{1-6})$alkylsulfonyl, $(C_{1-6})$haloalkylsulfonyl, aryl, haloaryl, alkoxyaryl, aryoxy, arylthio, haloaryloxy, heteroaryl, heteroaryloxy and $(C_{3-7})$cycloalkyl;

$R_5$ and $R_6$ are independent of each other and may be selected from the group consisting of $(C_{1-6})$alkyl, $(C_{2-6})$alkenyl, $(C_{2-6})$alkynyl, $(C_{1-6})$alkoxycarbonyl and heteroarylcarbonyl; where any of these groups may be optionally substituted with one or more of the following groups consisting of halogen, hydroxy, cyano, nitro, amino, caboxyl, $(C_{1-6})$alkyl, $(C_{1-6})$haloalkyl, $(C_{1-6})$alkylcarbonyl, $(C_{1-6})$alkylcarbonyloxy, $(C_{1-6})$haloalkylcarbonyl, $(C_{1-6})$haloalkylcarbonyloxy, $(C_{1-6})$alkoxy, $(C_{1-6})$alkoxycarbonyl, aminocarbonyl, $(C_{1-6})$alkylaminocarbonyl, $(C_{1-6})$haloalkoxy, $(C_{1-6})$haloalkoxycarbonyl, $(C_{1-6})$alkylsulfonyl, $(C_{1-6})$haloalkylsulfonyl, aryl, heteroaryl and $(C_{3-7})$cycloalkyl;

$R_7$ may be selected from the group consisting of hydrogen, $(C_{1-6})$alkyl, $(C_{2-6})$alkenyl or $(C_{2-6})$alkynyl;

Q is selected from $Q_1$, $Q_3$, $Q_5$, $Q_7$, $Q_9$ or $Q_{10}$;

wherein $A_1$ and $A_2$ are independently oxygen or sulfur;

$R_8$ is hydrogen, $(C_{1-4})$alkyl, $(C_{1-4})$haloalkyl, amino;

$R_9$ and $R_{10}$ are independent of each other and may be selected from the group consisting of hydrogen, halogen, cyano, $(C_{1-4})$alkyl, $(C_{1-4})$haloalkyl, $(C_{1-4})$alkoxy, $(C_{1-4})$haloalkoxy, $(C_{2-6})$alkenyl, $(C_{2-6})$haloalkenyl.

$R_{13}$ may be selected from the group consisting of hydrogen, halogen, $(C_{1-4})$alkyl, $(C_{1-4})$alkoxy, $(C_{1-4})$haloalkoxy, $(C_{1-4})$alkylthio, $(C_{1-4})$haloalkylthio, $(C_{1-4})$alkylsulfinyl, $(C_{1-4})$haloalkylsulfinyl; $(C_{1-4})$alkylsulfonyl or $(C_{1-4})$haloalkylsulfonyl, G' is carbonyl, $NR_{14}$, oxygen, $S(O)_{n^{**}}$ or $CR_{15}R_{16}$;

$R_{14}$ is hydrogen or $(C_{1-6})$alkyl;

$R_{15}$ and $R_{16}$ are independent of each other and may be selected from the group consisting of hydrogen, halogen, hydroxy, amino, cyano, $(C_{1-6})$alkyl, $(C_{1-6})$haloalkyl, $(C_{1-6})$alkoxy,$(C_{1-6})$haloalkoxy, $(C_{1-6})$alkoxyalkyl, $(C_{2-6})$alkynyl, $(C_{2-6})$alkenyl, aryl, heteroaryl, aryloxy, heteroaryloxy, $(C_{3-6})$cycloalkyl, $(C_{3-6})$cyclocarbonyl, carboxy, $(C_{1-6})$alkylcarbonyl, arylcarbonyl, $(C_{1-3})$haloalkylcarbonyl, $(C_{1-6})$alkylcarbonyloxy, $(C_{1-6})$haloalkylcarbonyloxy, $(C_{1-6})$alkoxycarbonyl, $(C_{1-6})$haloalkoxycarbonyl, $(C_{1-6})$alkylthiocarbonyl, $(C_{1-6})$haloalkylthiocarbonyl, $(C_{1-6})$alkoxythiocarbonyl, $(C_{1-6})$haloalkoxythiocarbonyl,$(C_{1-6})$alkylamino, arylsulfonylamino, arylamino, $(C_{1-3})$alkylthio, arylthio, $(C_{2-6})$alkenylthio, $(C_{2-6})$alkynylthio, $(C_{1-6})$alkylsulfinyl, $(C_{2-6})$alkenylsulfinyl, $(C_{2-6})$alkynylsulfinyl, $(C_{1-6})$alkylsulfonyl, $(C_{2-6})$alkenylsulfonyl, $(C_{2-6})$alkynylsulfonyl, arylsulfonyl, where any of these groups may be optionally substituted with one or one more of the following group consisting of halogen, hydroxy, mercapto, cyano, nitro, amino, caboxyl, $(C_{1-6})$alkyl, $(C_{1-6})$haloalkyl, $(C_{1-6})$alkylcarbonyl, $(C_{1-6})$alkylcarbonyloxy, $(C_{1-6})$haloalkylcarbonyl, $(C_{1-6})$haloalkylcarbonyloxy, $(C_{1-6})$alkoxy, $(C_{1-6})$alkoxycarbonyl, aminocarbonyl, $(C_{1-6})$alkylaminocarbonyl, $(C_{1-6})$haloalkoxy, $(C_{1-6})$haloalkoxycarbonyl, $(C_{1-6})$alkylsulfonyl, $(C_{1-6})$haloalkylsulfonyl, aryl, heteroaryl and $(C_{3-7})$cycloalkyl;

n and m are independent of each other and represent an integer from 0 to 2; provided that m+n is 2, 3 or 4;

n** is represent an integer from 0 to 2;

The most preferred formula (I) compounds of this invention are those wherein

X and Y are independent of each other represent hydrogen or halogen;

T is CH;

Z is selected from group (II) or (V);

A is oxygen;

$R_1$, $R_2$, $R_3$ and $R_4$ are independent of each other and may be selected from the group consisting of hydrogen, $(C_{1-6})$alkyl, $(C_{1-6})$haloalkyl, $(C_{1-6})$alkoxy,$(C_{1-6})$haloalkoxy, $(C_{1-6})$alkoxyalkyl, $(C_{2-6})$alkynyl, $(C_{2-6})$alkenyl, aryl, heteroaryl, aryloxy, heteroaryloxy, $(C_{3-6})$cycloalkyl, $(C_{3-6})$cyclocarbonyl, carboxy, $(C_{1-6})$alkylcarbonyl, arylcarbonyl, $(C_{1-3})$, $(C_{1-6})$alkoxycarbonyl, $(C_{1-6})$haloalkoxycarbonyl, $(C_{1-6})$alkylthiocarbonyl, $(C_{1-6})$alkoxythiocarbonyl, $(C_{1-6})$alkylamino, arylsulfonylamino, arylamino, $(C_{1-6})$alkylthio, arylthio, $(C_{2-6})$alkenylthio, $(C_{1-6})$alkylsulfinyl, $(C_{2-6})$alkenylsulfinyl, $(C_{2-6})$alkynylsulfinyl, $(C_{1-6})$alkylsulfonyl, $(C_{2-6})$alkenylsulfonyl, arylsulfonyl, $R_5$ and $R_6$ are independent of each other and may be selected from the group consisting of $(C_{1-6})$alkyl, $(C_{2-6})$alkenyl, $(C_{2-6})$alkynyl;

$R_7$ may be selected from the group consisting of hydrogen, $(C_{1-6})$alkyl, $(C_{2-6})$alkenyl or $(C_{2-6})$alkynyl;

Q is selected from $Q_1$, $Q_3$ or $Q_5$;

wherein $A_1$ and $A_2$ are oxygen;

$R_8$ is $(C_{1-4})$alkyl, $(C_{1-4})$haloalkyl, amino;

$R_9$ and $R_{10}$ are independent of each other and may be selected from the group consisting of hydrogen, $(C_{1-4})$alkyl, $(C_{1-4})$haloalkyl, $(C_{1-4})$alkoxy, $(C_{1-4})$haloalkoxy, $(C_{2-6})$alkenyl, $(C_{2-6})$haloalkenyl;

$R_{13}$ may be selected from the group consisting of hydrogen, halogen, cyano, $(C_{1-4})$alkoxy, $(C_{1-4})$haloalkoxy, hydroxy;

Some compounds of this formula (I) may form a salt with organic and inorganic acids, propargyl and allyl halides, dimethyl sulfate, etc. A salt of compound represented by the formula (I) may contain cases that Z is group VI or VII in formula (I).

In the definitions given above, unless alkyl, alkenyl, alkynyl and halogen are defined or mentioned, the term alkyl used either alone or in compound words such as "haloalkyl" or "alkylcarbonyl" includes straight-chain or branched chains containing 1 to 6 carbon atoms. The terms of alkenyl and alkynyl include straight chain or branched alkenes and alkynes respectively containing 2 to 6 carbon atoms, and the term halogen either alone or in the compound words such as haloalkyl indicates fluorine, chlorine, bromine, or iodine.

Further a haloalkyl is represented by an alkyl partially or fully substituted with halogen atoms which may be same or different. The term or part of the term "aryl" or "heteroaryl" are defined as those monocyclic or fused bicyclic aromatic rings wherein at least one ring satisfy the Hückel rule and contain 0 to 4 heteroatoms, examples include: phenyl, furyl, furazanyl, thienyl, pyrrolyl, pyrazolyl, oxazolyl, oxadiazolyl, imidazolyl, isoxazolyl, thiazolyl, thiadiazolyl, isothiazolyl, tetrazolyl, pyridinyl, pyrimidinyl, pyridazinyl, pyrazinyl, triazinyl, quinolyl, isoquinolyl, quinoxalinyl, benzofuranyl, 2,3-dihydrobenzofuranyl, isobenzofuranyl, benzothienyl, benzodioxolyl, chromanyl, indolinyl, isoindolyl, naphthyl, thienofuranyl and purinyl. These rings can attached through any available carbon or nitrogen, for example, when the aromatic ring system is furyl, it can be 2-furyl or 3-furyl, for pyrrolyl, the aromatic ring system is 1-pyrrolyl, 2-pyrrolyl or 3-pyrrolyl, for naphthyl, the carbobicyclic aromatic ring is 1-naphthyl or 2-naphthyl and for benzofuranyl, the aromatic ring system can be 2-, 3-, 4-, 5-, 6- or 7-benzofuranyl.

DETAILED DESCRIPTION OF THE INVENTION

The compounds described by the formula (I) can be prepared by the procedures as described herein. Using commercially available starting materials or those whose synthesis is known in the art, the compounds of this invention may be prepared using methods described in the following Schemes, or using modifications thereof, which are within the scope of the art.

The starting carboxylic acid represented by formula (VIII) in Scheme 1 can be prepared according to the literature procedure (WO8810254). The carboxylic acid was converted to the corresponding acid halide represented by formula (IX) by treatment with halogenation agents such as thionyl chloride or oxalyl chloride with or without solvent at a temperature between 0° C. and 100° C. for 0.5 to 12 hours. Examples of solvent for this reaction include halogenated alkyl solvents such as dichloromethane, chloroform, or aromatic sovents such as benzene, toluene, xylene, etc. The solvent was removed under reduced pressure, then isolated and purified. Formula (XI) can be prepared by the condensation reaction of formula (IX) with the corresponding hydrazine derivatives represented by formula (X). The reaction was carried out with or without base such as triethyl amine or 1,8-diazabicyclo[5.4.0]undec-7-ene (DBU) at a temperature between 0° C. and 100° C. for 0.5 to 24 hours. The described procedure in Scheme 1 can also be applied to the synthesis of thiobenzohydrazide analogs of formula (XI).

SCHEME 1

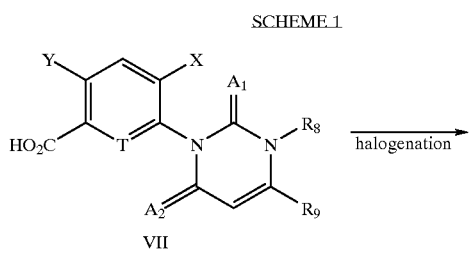

VII

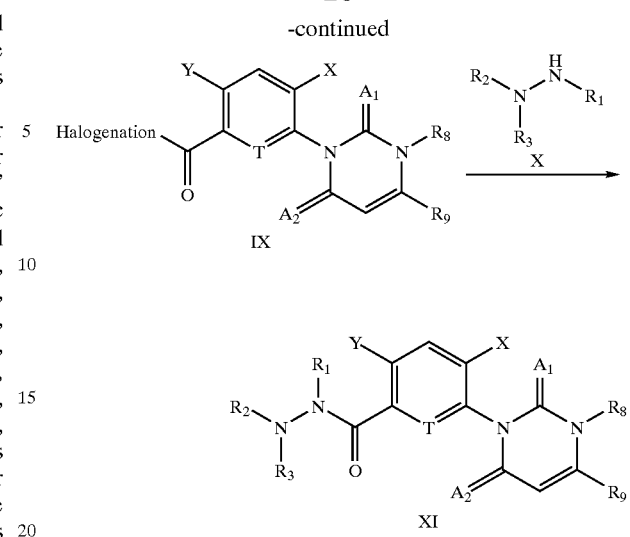

IX

XI

The product represented by formula (XIII) in Scheme 2 can be prepared from formula (XII) by treatment with an electrophile such as dimethyl sulfide in the presence of base such as potassium carbonate in an inert solvent such as acetone or toluene. The reaction can be carried out at a temperature between 0° C. and 200° C. for 0.5 to 48 hours.

SCHEME 2

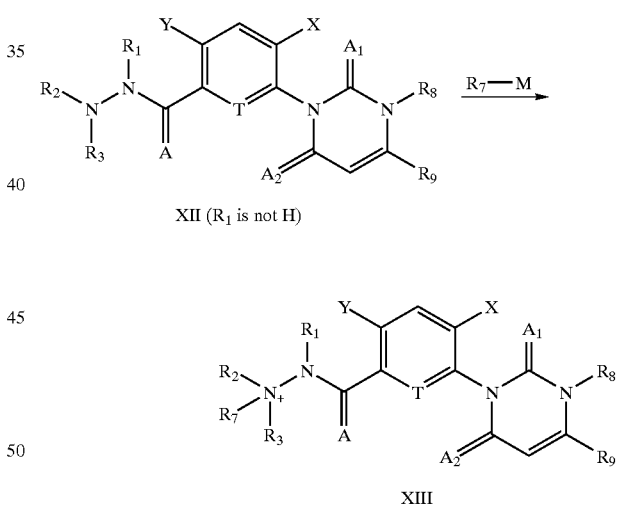

XII ($R_1$ is not H)

XIII

The compounds represented by the formula (XII) and (XIV) in Scheme 3 can be prepared from the corresponding compounds represented by formula (XII') by treatment with an electrophile such as methyl iodide or acetyl chloride in an inert solvent such as dioxane in the presence of base such as potassium carbonate. Formula (XII) or (XIV) can be converted to the corresponding quaternary salt derivatives represented by formula (XIII) or (XV). The reaction can be carried out according to the general procedure described in Scheme 2.

SCHEME 3

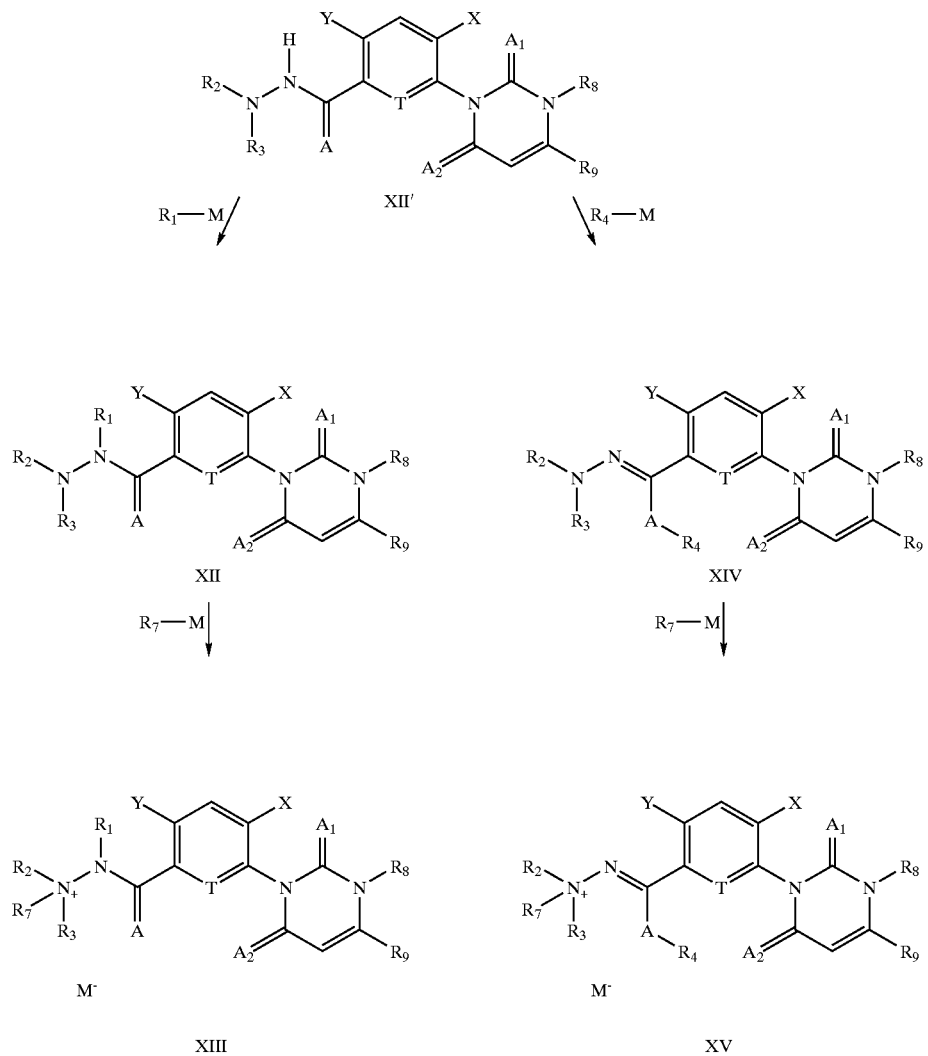

The compound represented in formula (XVI) in Scheme 4 can be prepared from formula (IX) by reaction with a corresponding hydrazone derivatives represented by formula (X') in an inert solvent such as tetrahydrofuran (THF) or toluene with or without base such as triethylamine, DBU or potassium carbonate at a temperature between 0° C. and 150° C. for 0.5 to 24 hours. The described procedure in Scheme 4 can also be applied to the synthesis of thiobenzohydrazide analogs of formula (X VI)

SCHEME 4

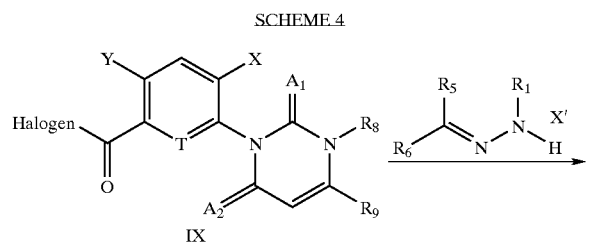

-continued

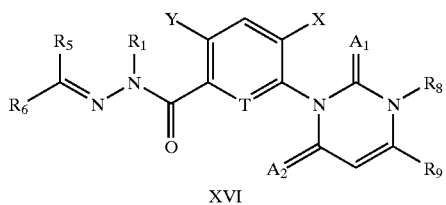

The substituted derivatives represented by the formula (XVI) and (XVIII) in Scheme 5 can be prepared from formula (XVII) by treatment with an electrophile such as methyl iodide or acetyl chloride. The reaction can be carried out in the presence of base such as triethylamine or potassium carbonate in an inert solvent such as 2-butenone at a temperature between 0° C. and 150° C. for 0.5 to 24 hours.

SCHEME 5

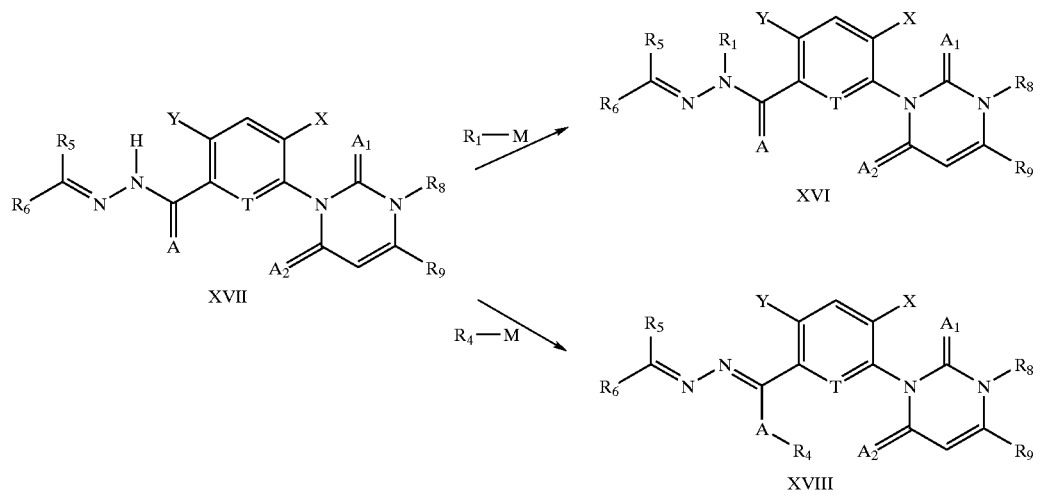

The compound represented by formula (XXII) in Scheme 6 can be prepared from formula (XXI) by the reaction with hydrazine with or without base such as potassium carbonate. The reaction can be carried out in an inert solvent such as toluene at a temperature between −10° C. to 150° C. for 0.5 to 24 hours. Formula (XVII) can be prepared from formula (XXII) by condensation reaction with aldehyde or ketone in an inert solvent such as DMF with or without catalyst such as p-toluenesulfonic acid or potassium carbonate at a temperature between −10° C. and 150° C. for 0.5 to 24 hours.

SCHEME 6

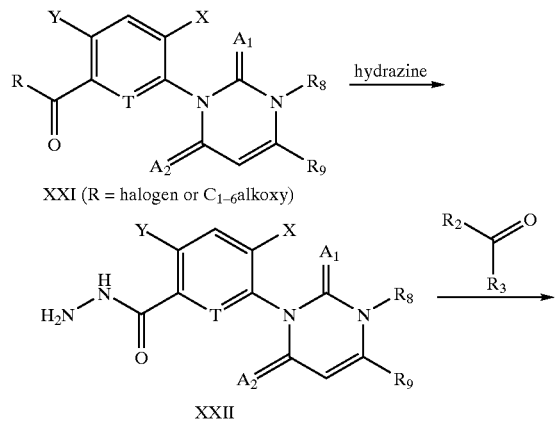

XXI (R = halogen or $C_{1-6}$alkoxy)

-continued

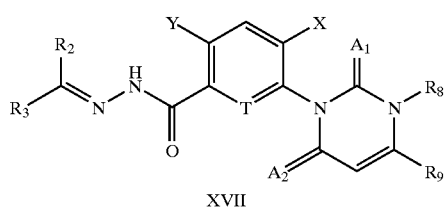

XVII

The compound represented by formula (XXIII) in Scheme 7 can be prepared according to the literature procedure (EP 361114). Formula (XXIV) can be prepared according to the general procedure described in Scheme 1. Formula (XXIV) is then converted into the corresponding sulfur analogue represented by formula (XXV) by treating typical reagent such as Lawesson's5 reagent. Formula (XXVI) or (XXVII) can be prepared according to the general procedures described in Scheme 2.

SCHEME 7

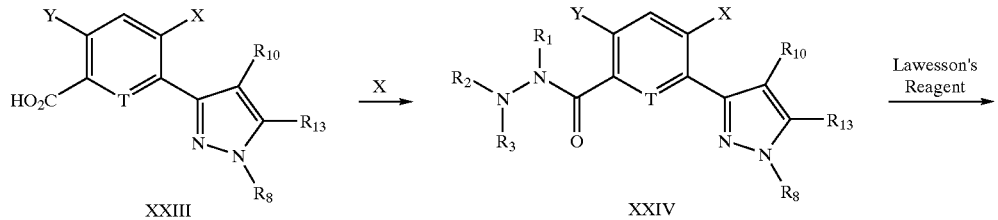

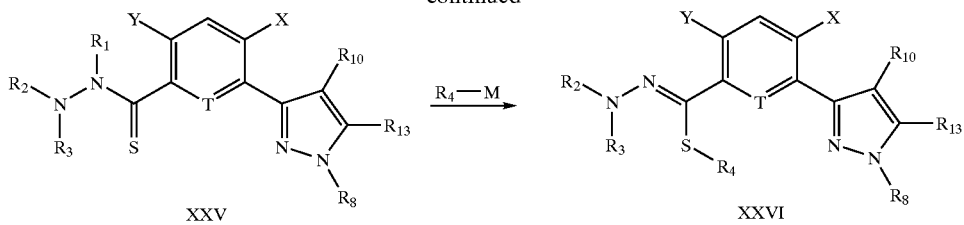

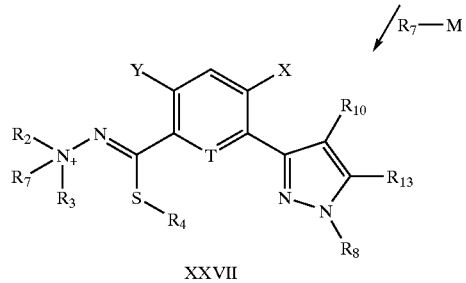

The compound represented by formula (XI) and (XVI) in Scheme 8 can be prepared from formula (VIII) by a coupling reaction with corresponding hydrazine derivative in the presence of a dehydration reagent such as 1,3-dicyclohexylcarbodiimide (DCC). The reaction can be carried out with or without base such as N,N-dimethylaminopyridine (DMAP) in an inert solvent such as dichloromethane at a temperature between −10° C. and 100° C. for 0.5 to 24 hours.

SCHEME 9

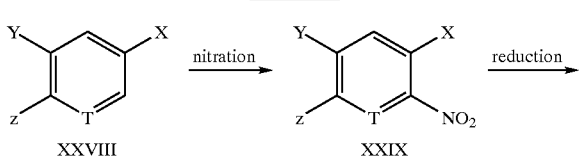

SCHEME 8

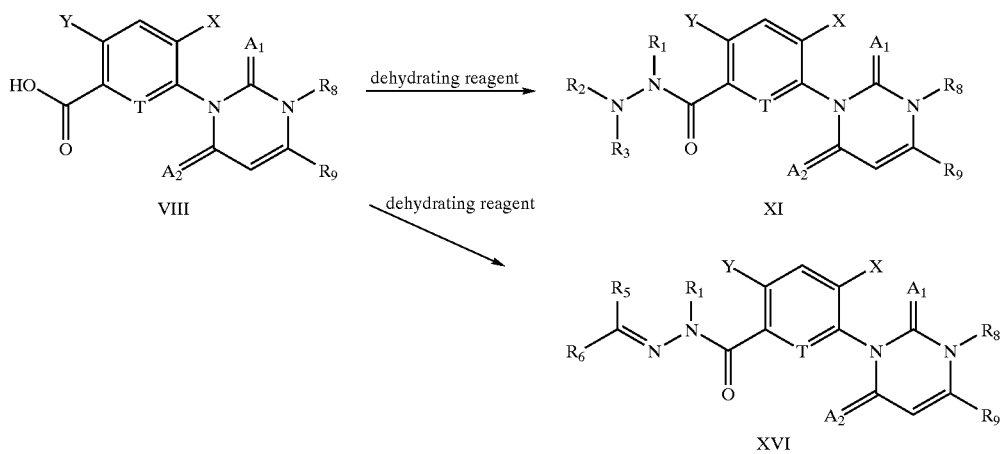

The compound represented by formula (XXIX) in Scheme 9 can be prepared from formula (XXVIII). Nitration can be carried out by treatment with a nitrating reagent such as nitric acid at a temperature between −30° C. and 60° C. for 0.5 to 6 hours. Formula (XXIX) is then converted into the corresponding aniline represented by formula (XXX) by typical reduction procedure e.g. iron in an acidic medium such as acetic acid or by catalytic hydrogenation. Uracil derivatives represented by formula (XXXII) can be prepared analogously by known method (U.S. Pat. No. 4,859,229).

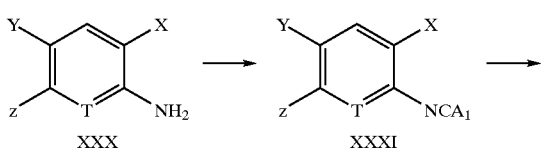

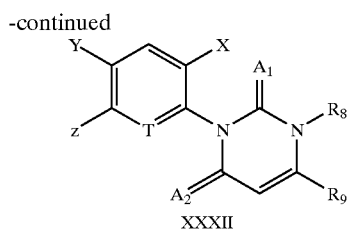

XXXII

EXAMPLE 1
Preparation of 2-chloro-5-(3,6-dihydro-3-methyl-2,6-dioxo-4-(trifluoromethyl)-1(2H)-pyrimidinyl)-N-[1-(1,1-dimethylethyl)-2,2-dimethylpropylidene]-4-fluoro-benzenecarbohydrazonic Acid Methyl Ester (Compound no. 5–6)

Step 1 Preparation of 2-chloro-5-(3,6-dihydro-3-methyl-2,6-dioxo-4-(trifluoromethyl)-1(2H)-pyrimidinyl)-4-fluoro-benzoic Acid 2-Chloro-5-(3,6-dihydro-3-methyl-2,6-dioxo-4-(trifluoromethyl)-1(2H)-pyrimidinyl)-4-fluoro-benzoic acid ethyl ester (5.2 g) was dissolved in methylenechloride (100 ml) and borontribromide (10 g) was added dropwise at ambient temperature. The reaction mixture was stirred for three hours at this temperature and poured into ice-water. The resulting mixture was extracted with ethyl acetate. The organic phase was washed with brine (×3) and dried over anhydrous $Na_2SO_4$. The solvent was removed under reduced pressure to give the titled compound (4.3 g) as a white solid.

Step 2 Preparation of 2-chloro-5-(3,6-dihydro-3-methyl-2,6-dioxo-4-(trifluoromethyl)-1(2H)-pyrimidinyl)-4-fluoro-benzoyl Chloride To a stirred solution of 2-chloro-5-(3,6-dihydro-3-methyl-2,6-dioxo-4-(trifluoromethyl)-1(2H)-pyrimidinyl)-4-fluoro-benzoic acid (4 g) in chloroform (100 ml) were added oxalyl chloride (1.8 g) and a few drops of N,N-dimethylformamide (DMF) at ambient temperature. The resulting mixture was stirred for three hours at same temperature and then filtered through Celite. The filtrate was concentrated under reduced pressure to give the titled compound (4.3 g) as a brown solid.

Step 3 Preparation of, 2-chloro-5-(3,6-dihydro-3-methyl-2,6-dioxo-4-(trifluoromethyl)-1(2H)-pyrimidinyl)-4-fluoro-benzoic acid, 2-[1-(1,1-dimethylethyl)-2,2-dimethylpropylidene]hydrazide (Compound No. 6-4)

2-Chloro-5-(3,6-dihydro-3-methyl-2,6-dioxo-4-(trifluoromethyl)-1(2H)-pyrimidinyl)-4-fluoro-benzoyl chloride (0.67 g) was dissolved in tetrahydrofuran (25 ml) and 3-pentanone, 2,2,4,4-tetramethyl-hydrazone (0.3 g) was added and the solution stirred overnight at ambient temperature. The reaction mixture was partitioned between ethyl acetate and brine. The organic phase was washed with brine (×3) and dried over anhydrous $Na_2SO_4$. The organic solvent was removed under reduced pressure and the residual oily product was purified by column chromatography on silica gel to give the titled compound (0.14 g).

Step 4

A mixed solution of 2-chloro-5-(3,6-dihydro-3-methyl-2,6-dioxo-4-(trifluoromethyl)-1(2H)-pyrimidinyl)-4-fluoro-benzoic acid, 2-[1-(1,1-dimethylethyl)-2,2-dimethylpropylidene]hydrazide (0.48 g), excess of methyl iodide and potassium carbonate (0.132 g) in acetonitrile (20 ml) was heated at reflux temperature overnight. The mixture was allowed to cool to ambient temperature and partitioned between ethyl acetate and brine. The organic phase was washed with brine (×3) and dried over anhydrous $Na_2SO_4$. The solvent was removed under reduced pressure and the residue was purified by column chromatography on silica gel eluted with a mixed solvent of ethyl acetate and hexane (1:4 to 1:2) to give the titled compound (0.25 g) along with its, 2-chloro-5-(3,6-dihydro-3-methyl-2,6-dioxo-4-(trifluoromethyl)-1(2H)-pyrimidinyl)-4-fluoro-benzoic acid, 2-[1-(1,1-dimethylethyl)-2,2-dimethylpropylidene]-1-methylhydrazide (0.1 g, Compound No. 6–8)

EXAMPLE 2
Preparation of 2-chloro-5-(3,6-dihydro-3-methyl-2,6-dioxo-4-(trifluoromethyl)-1(2H)-pyrimidinyl)-4-fluoro-benzoic Acid, 2-(1,1-dimethylethyloxy)carbonyl Hydrazide (Compound No.1–24)

To a solution of 2-chloro-5-(3,6-dihydro-3-methyl-2,6-dioxo-4-(trifluoromethyl)-1(2H)-pyrimidinyl)-4-fluoro-benzoyl chloride (0.5 g) in tetrahydrofuran (20 ml) was added t-butylcarbazate (0.18 g) at ambient temperature. After 1 hour, the resulting mixture was concentrated under reduced pressure and the residue was subjected to column chromatography on silica gel eluted with a mixed solvent of ethyl acetate and hexane (2:3) to give the titled compound (0.48 g).

EXAMPLE 3
Preparation of, 2-chloro-5-(3,6-dihydro-3-methyl-2,6-dioxo-4-(trifluoromethyl)-1(2H)-pyrimidinyl)-4-fluoro-N-(1,2,2-trimethylpropylidene)-benzenecarbohydrazonic Acid, Acetyl Ester (Compound No. 5-2)

Step 1 Preparation of 2-chloro-5-(3,6-dihydro-3-methyl-2,6-dioxo-4-(trifluoromethyl)-1(2H)-pyrimidinyl)-4-fluoro-benzoic Acid, 2-(1,2,2-trimethylpropylidene)hydrazide (Compound No. 6-5)

Oxalyl chloride (2.2 ml, 25.0 mmol) was added dropwise to a solution of 2-chloro-5-(3,6-dihydro-3-methyl-2,6-dioxo-4-(trifluoromethyl)-1(2H)-pyrimidinyl)-4-fluoro-benzoic acid (3.0 g) in toluene (30 ml) with DMF (0.1 ml). The reaction was heated at reflux for 1 hour, and filtered through Celite. The filtrate was concentrated under reduced pressure and re-dissolved in toluene (50 ml). To this solution was added a solution of 3,3-dimethylbutan-2-one hydrazone (9.74 g) and triethylamine (1.2 ml) in toluene (5 ml) at 0° C. The reaction mixture was allowed to warm to ambient temperature and stirred for 30 minutes. The resulting solution was diluted with ethyl acetate and washed with saturated ammonium chloride solution (×1). The organic phases were separated and the aqueous phase was extracted with ethyl acetate (×1). The combined organic layers were dried over anhydrous $MgSO_4$ and concentrated under reduced pressure to give an oily material. The crude product was purified by column chromatography on silica gel eluted with a mixed solvent of methanol and methylene chloride (3:97) to give the titled compound (2.62 g) as a colorless oil.

Step 2

Acetyl chloride (0.05 mL, 0.70 mmol) was added to a solution of 2-chloro-5-(3,6-dihydro-3-methyl-2,6-dioxo-4-(trifluoromethyl)-1(2H)-pyrimidinyl)-4-fluoro-benzoic acid, 2-(1,2,2-trimethylpropylidene)hydrazide (0.30 g) and triethylamine (0.10 ml) in methylene chloride (20 ml) at 0° C. The reaction solution was stirred for 2 hours at ambient temperature. The solvent was removed under reduced pressure and the residue was purified by column chromatography on silica gel eluted with a mixed solvent of ethyl acetate and hexane (30:70) to give the titled compound (0.30 g) as a white solid.

TABLE 1

| Compd. No. | X | Y | R₁ | R₂ | R₃ | A | A₁ | R₈ |
|---|---|---|---|---|---|---|---|---|
| 1-1 | H | Cl | H | H | Me | O | O | Me |
| 1-2 | H | Cl | H | H | Ph | O | O | NH₂ |
| 1-3 | H | Cl | H | H | Ph | O | O | Me |
| 1-4 | H | Cl | H | Me | Me | O | O | Me |
| 1-5 | F | Cl | H | Me | Me | O | O | Me |
| 1-6 | F | Cl | Me | Me | Me | O | O | Me |
| 1-7 | F | Cl | Ph | H | Ph | O | S | Me |
| 1-8 | F | Cl | Ph | H | Ph | O | O | Me |
| 1-9 | F | Cl | H | Me | Ph | O | O | Me |
| 1-10 | F | Cl | H | Et | Et | O | O | Me |
| 1-11 | F | Cl | H | —(CH₂)₄— | | O | O | Me |
| 1-12 | F | Br | H | —(CH₂)₄— | | O | O | NH₂ |
| 1-13 | F | Br | H | —(CH₂)₄— | | O | O | Me |
| 1-14 | F | Cl | H | —(CH₂)₂NMe(CH₂)₂— | | O | S | Me |
| 1-15 | F | Cl | H | —CHMe(CH₂)₃CHMe— | | O | S | Me |
| 1-16 | F | Cl | H | —CHMe(CH₂)₃CHMe— | | O | O | Me |
| 1-17 | F | Br | H | —(CH₂)₅— | | O | O | Me |
| 1-18 | H | Cl | H | Ph | H | S | O | Me |
| 1-19 | Cl | Cl | H | 2-pyridyl | Me | O | O | Me |
| 1-20 | F | Cl | H | 2-pyrimidyld | Et | NH | O | Me |
| 1-22 | F | Cl | H | t-Bu | t-Bu | O | O | Me |
| 1-23 | F | Cl | H | H | C(O)OEt | O | O | Me |
| 1-24 | F | Cl | H | H | C(O)OtBu | O | O | Me |
| 1-25 | F | Cl | Me | Me | C(O)OtBu | O | O | Me |
| 1-26 | H | Cl | H | H | Ac | O | O | Me |
| 1-27 | H | CF₃ | H | Me | Me | O | O | Me |
| 1-28 | F | MeO | H | —C(O)(CH₂)₃— | | S | O | Me |
| 1-29 | F | Cl | H | Bn | Bn | O | O | Me |
| 1-30 | F | Cl | H | Ph | Ph | O | O | Me |

TABLE 2

| Compd. No. | X | Y | R₁ | R₂ | R₃ | A | A₁ |
|---|---|---|---|---|---|---|---|
| 2-1 | H | Cl | H | H | Me | O | O |
| 2-2 | H | Cl | H | H | Ph | O | O |
| 2-3 | H | Cl | H | H | Ph | O | O |
| 2-4 | F | Cl | H | Me | Me | O | O |
| 2-5 | F | Cl | Me | Me | Me | O | O |
| 2-6 | F | Cl | Ph | H | Ph | O | S |
| 2-7 | F | Cl | Ph | H | Ph | O | O |
| 2-8 | F | Cl | H | Me | Ph | O | O |
| 2-9 | F | Cl | H | Et | Et | O | O |
| 2-10 | F | Br | H | —(CH₂)₄— | | O | O |
| 2-11 | F | Br | H | —(CH₂)₄— | | O | O |
| 2-12 | F | Cl | H | —CHMe(CH₂)₃CHMe— | | O | O |
| 2-13 | F | Br | H | —(CH₂)₅— | | O | O |
| 2-14 | H | Cl | H | Ph | H | S | O |
| 2-15 | Cl | Cl | H | 2-pyridyl | Me | O | O |
| 2-16 | F | Cl | H | 2-pyrimidyl | Et | NH | O |
| 2-18 | F | Cl | H | t-Bu | t-Bu | O | O |
| 2-19 | F | Cl | H | H | C(O)OEt | O | O |
| 2-20 | F | Cl | H | H | C(O)OtBu | O | O |
| 2-21 | H | Cl | H | H | Ac | O | O |
| 2-22 | H | CF₃ | H | Me | Me | O | O |
| 2-23 | F | MeO | H | —C(O)(CH₂)₃— | | S | O |
| 2-24 | F | Cl | H | Bn | Bn | O | O |

TABLE 3

| Compd. No. | X | Y | R$_1$ | R$_2$ | R$_3$ | A | R$_{13}$ | R$_{10}$ |
|---|---|---|---|---|---|---|---|---|
| 3-1 | H | Cl | H | H | Me | O | OCHF$_2$ | Cl |
| 3-2 | H | Cl | H | H | Ph | O | SCHF$_2$ | Cl |
| 3-3 | H | Cl | H | H | Ph | O | OCHF$_2$ | Cl |
| 3-4 | F | Cl | H | Me | Me | O | OCF$_3$ | Cl |
| 3-5 | F | Cl | H | Me | Me | O | OCH$_2$CF$_3$ | Cl |
| 3-6 | F | Cl | H | Me | Me | O | OCHF$_2$ | Cl |
| 3-7 | H | Cl | H | Me | Me | O | OCHF$_2$ | CN |
| 3-8 | F | Cl | Me | Me | Me | O | OCHF$_2$ | Cl |
| 3-9 | F | Cl | H | Me | Me | O | OCHF$_2$ | Br |
| 3-10 | F | Cl | Ph | H | Ph | O | OCHF$_2$ | Cl |
| 3-11 | F | Cl | H | Me | Ph | O | OCHF$_2$ | Cl |
| 3-12 | F | Cl | H | Et | Et | O | OCHF$_2$ | Cl |
| 3-13 | F | Br | H | —(CH$_2$)$_4$— | | O | OCHF$_2$ | Cl |
| 3-14 | F | Br | H | —(CH$_2$)$_4$— | | O | OCHF$_2$ | Cl |
| 3-15 | F | Cl | H | —CHMe(CH$_2$)$_3$CHMe— | | O | OCHF$_2$ | Cl |
| 3-16 | F | Br | H | —(CH$_2$)$_5$— | | O | OCHF$_2$ | Cl |
| 3-17 | H | Cl | H | Ph | H | S | OCHF$_2$ | Cl |
| 3-18 | Cl | Cl | H | 2-pyridyl | Me | O | OCHF$_2$ | Cl |
| 3-19 | F | Cl | H | t-Bu | t-Bu | O | OCHF$_2$ | Cl |
| 3-20 | F | Cl | H | H | C(O)OEt | O | OCHF$_2$ | Cl |
| 3-21 | F | Cl | H | H | C(O)OtBu | O | OCHF$_2$ | Cl |
| 3-22 | H | Cl | H | H | Ac | O | OCHF$_2$ | Cl |
| 3-23 | H | CF$_3$ | H | Me | Me | O | OCHF$_2$ | Cl |

TABLE 4

| Compd. No. | X | Y | R$_2$ | R$_3$ | R$_4$ | A | A$_1$ | R$_8$ |
|---|---|---|---|---|---|---|---|---|
| 4-1 | F | Cl | Me | Me | Me | O | O | NH$_2$ |
| 4-2 | F | Cl | Me | Me | Me | O | S | Me |
| 4-3 | H | Cl | Me | Me | Me | O | O | Me |
| 4-4 | H | Cl | Me | Me | Ac | O | O | Me |
| 4-5 | F | Cl | Me | Me | Ac | O | O | Me |
| 4-6 | F | Cl | Me | Me | C(O)CHCl$_2$ | O | O | Me |
| 4-7 | F | Cl | Me | Me | SO$_2$Me | O | O | Me |
| 4-8 | F | Cl | —CHMe(CH$_2$)$_3$CHMe— | | COCHCl$_2$ | O | O | Me |
| 4-9 | F | Cl | —CHMe(CH$_2$)$_3$CHMe— | | Ac | O | O | Me |
| 4-10 | Cl | Cl | —(CH$_2$)$_4$— | | Ac | O | O | Me |
| 4-11 | Cl | Cl | —(CH$_2$)$_4$— | | Me | S | O | Me |
| 4-12 | F | Cl | Ph | Me | Me | O | O | Me |
| 4-13 | F | Cl | Me | Me | Propargyl | O | O | Me |

TABLE 5

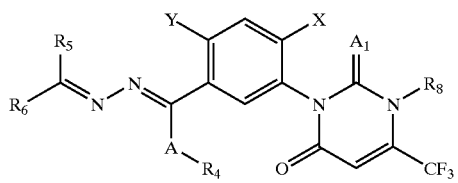

| Compd. No. | X | Y | R$_4$ | R$_5$ | R$_6$ | A | A$_1$ | R$_8$ |
|---|---|---|---|---|---|---|---|---|
| 5-1 | F | Cl | Me | t-Bu | Me | O | O | Me |
| 5-2 | F | Cl | Ac | t-Bu | Me | O | O | Me |
| 5-3 | F | Cl | SO$_2$Me | t-Bu | Me | O | O | Me |
| 5-4 | F | Cl | COCHCl$_2$ | t-Bu | Me | O | O | Me |
| 5-5 | H | Cl | Me | t-Bu | Me | O | O | Me |
| 5-6 | F | Cl | Me | t-Bu | t-Bu | O | O | Me |
| 5-7 | F | Cl | Propargyl | t-Bu | t-Bu | O | O | Me |
| 5-8 | Cl | Cl | Propargyl | Et | t-Bu | O | O | Me |
| 5-9 | F | Cl | Me | —(CH$_2$)$_4$— | | O | O | Me |
| 5-10 | F | Cl | Benzoyl | Me | Me | O | O | Me |
| 5-11 | F | CF$_3$ | Ac | t-Bu | t-Bu | O | O | Me |
| 5-12 | F | Cl | Me | —CO(CH$_2$)$_2$CO— | | O | O | Me |
| 5-13 | F | Cl | Ac | —CHMe(CH$_2$)$_3$CHMe— | | O | O | Me |
| 5-14 | F | Cl | COCHCl$_2$ | —CHMe(CH$_2$)$_3$CHMe— | | O | O | Me |
| 5-15 | F | Cl | Allyl | —CHMe(CH$_2$)$_3$CHMe— | | O | O | Me |
| 5-16 | F | Br | Me | t-Bu | t-Bu | S | O | Me |

TABLE 6

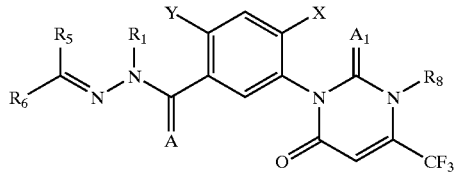

| Compd. No. | X | Y | R$_1$ | R$_5$ | R$_6$ | A | A$_1$ | R$_8$ |
|---|---|---|---|---|---|---|---|---|
| 6-1 | H | Cl | H | Me | Me | O | O | Me |
| 6-2 | F | Cl | H | t-Bu | t-Bu | O | S | Me |
| 6-3 | F | Cl | H | t-Bu | t-Bu | O | O | NH$_2$ |
| 6-4 | F | Cl | H | t-Bu | t-Bu | O | O | Me |
| 6-5 | F | Cl | H | t-Bu | Me | O | O | Me |
| 6-6 | F | Cl | Ac | t-Bu | Me | O | O | Me |
| 6-7 | H | Cl | H | t-Bu | t-Bu | O | O | Me |
| 6-8 | F | Cl | Me | t-Bu | t-Bu | O | O | Me |
| 6-9 | H | Cl | H | t-Bu | Me | O | O | Me |

TABLE 6-continued

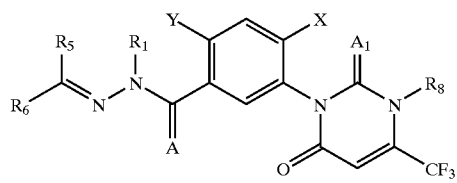

| Compd. No. | X | Y | R$_1$ | R$_5$ | R$_6$ | A | A$_1$ | R$_8$ |
|---|---|---|---|---|---|---|---|---|
| 6-10 | F | Cl | H | 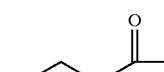 | | O | O | Me |
| 6-11 | F | Cl | H | —(CH$_2$)$_4$— | | O | O | Me |
| 6-12 | F | Cl | Me | —CO(CH$_2$)$_2$CO— | | O | O | Me |
| 6-13 | F | Cl | Allyl | —CHMe(CH$_2$)$_3$CHMe— | | O | O | Me |
| 6-14 | F | Br | Me | t-Bu | t-Bu | S | O | Me |
| 6-15 | F | Cl | H | Ph | Ph | O | O | Me |

TABLE 7

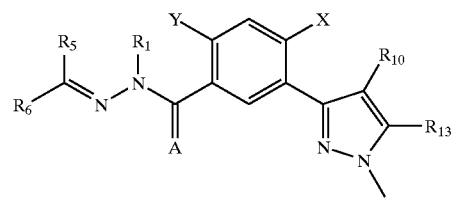

| Compd. No. | X | Y | R$_1$ | R$_5$ | R$_6$ | A | R$_{13}$ | R$_{10}$ |
|---|---|---|---|---|---|---|---|---|
| 7-1 | H | Cl | H | t-Bu | t-Bu | O | OCHF$_2$ | Cl |
| 7-2 | F | Cl | H | t-Bu | t-Bu | O | OCHF$_2$ | Cl |
| 7-3 | H | Cl | H | t-Bu | t-Bu | O | SCHF$_2$ | Cl |
| 7-4 | F | Cl | H | t-Bu | Me | O | OCHF$_2$ | Cl |
| 7-5 | H | Cl | H | t-Bu | Me | O | OCHF$_2$ | CN |
| 7-6 | F | Cl | Me | t-Bu | t-Bu | O | OCHF$_2$ | Cl |
| 7-7 | F | Cl | H | t-Bu | t-Bu | O | OCHF$_2$ | Br |
| 7-8 | F | Cl | Ph | t-Bu | Me | O | OCHF$_2$ | Cl |
| 7-9 | F | Cl | H | Me | Ph | O | OCHF$_2$ | Cl |
| 7-10 | F | Cl | H | Et | Et | O | OCHF$_2$ | Cl |
| 7-11 | F | Br | H | —(CH$_2$)$_4$— | | O | OCHF$_2$ | Cl |
| 7-12 | F | Br | H | —(CH$_2$)$_4$— | | O | OCHF$_2$ | Cl |
| 7-13 | F | Cl | H | —CHMe(CH$_2$)$_3$CHMe— | | O | OCHF$_2$ | Cl |
| 7-14 | F | Br | H | —(CH$_2$)$_5$— | | O | OCHF$_2$ | Cl |
| 7-15 | H | Cl | H | Ph | H | S | OCHF$_2$ | Cl |

TABLE 8

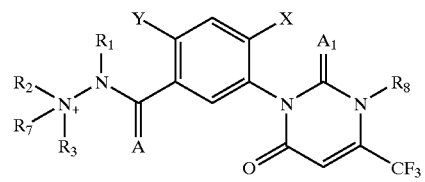

| Compd. No. | X | Y | R$_1$ | R$_2$ | R$_3$ | R$_7$ | A | A$_1$ | R$_8$ |
|---|---|---|---|---|---|---|---|---|---|
| 8-1 | H | Cl | H | H | Me | Me | O | O | Me |
| 8-2 | H | Cl | H | H | Ph | Me | O | O | Me |

TABLE 8-continued

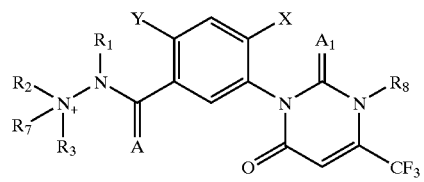

| Compd. No. | X | Y | R₁ | R₂ | R₃ | R₇ | A | A₁ | R₈ |
|---|---|---|---|---|---|---|---|---|---|
| 8-3 | F | Cl | H | Me | Me | Me | O | O | Me |
| 8-4 | F | Cl | H | Me | Me | Bn | O | O | Me |
| 8-5 | F | Cl | Me | Me | Me | Me | O | O | NH₂ |
| 8-6 | F | Cl | Me | Me | Me | Me | O | S | Me |
| 8-7 | F | Cl | Me | Me | Me | Me | O | O | Me |
| 8-8 | F | Cl | Ph | H | Ph | Me | O | O | Me |
| 8-9 | F | Cl | H | Me | Ph | Me | O | O | Me |
| 8-10 | F | Cl | H | Et | Et | Allyl | O | O | Me |
| 8-11 | F | Br | H | —(CH₂)₄— | | Me | O | O | Me |
| 8-12 | F | Cl | H | —CHMe(CH₂)₃CHMe— | | Me | O | O | Me |
| 8-13 | F | Br | H | —(CH₂)₅— | | Me | O | O | Me |
| 8-14 | H | Cl | H | Ph | H | Me | S | O | Me |
| 8-15 | Cl | Cl | H | 2-pyridyl | Me | Me | O | O | Me |
| 8-16 | F | Cl | H | 2-pyrimidyl | Et | Me | NH | O | Me |
| 8-17 | F | Cl | H | t-Bu | t-Bu | Me | O | O | Me |
| 8-18 | F | Cl | H | H | C(O)OEt | Me | O | O | Me |
| 8-19 | F | Cl | H | H | C(O)OtBu | Me | O | O | Me |
| 8-20 | H | Cl | H | H | Ac | Me | O | O | Me |
| 8-21 | H | CF₃ | H | Me | Me | Me | O | O | Me |
| 8-22 | F | MeO | H | —C(O)(CH₂)₃— | | Me | S | O | Me |
| 8-23 | F | Cl | H | Bn | Bn | Me | O | O | Me |

TABLE 9

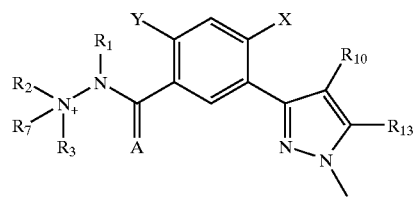

| Compd. No. | X | Y | R₁ | R₂ | R₃ | R₇ | A | R₁₃ | R₁₀ |
|---|---|---|---|---|---|---|---|---|---|
| 9-1 | H | Cl | H | H | Me | Me | O | OCHF₂ | Cl |
| 9-2 | H | Cl | H | H | Ph | Me | O | OCHF₂ | Cl |
| 9-3 | F | Cl | H | Me | Me | Me | O | OCHF₂ | Cl |
| 9-4 | F | Cl | H | Me | Me | Bn | O | OCHF₂ | Cl |
| 9-5 | F | Cl | Me | Me | Me | Me | O | SCHF₂ | Cl |
| 9-6 | F | Cl | Me | Me | Me | Me | O | OCHF₂ | CN |
| 9-7 | F | Cl | Me | Me | Me | Me | O | OCHF₂ | Cl |
| 9-8 | F | Cl | Ph | H | Ph | Me | O | OCHF₂ | Cl |
| 9-9 | F | Cl | H | Me | Ph | Me | O | OCHF₂ | Cl |
| 9-10 | F | Cl | H | Et | Et | Allyl | O | OCHF₂ | Cl |
| 9-11 | F | Br | H | —(CH₂)₄— | | Me | O | OCHF₂ | Cl |
| 9-12 | F | Cl | H | —CHMe(CH₂)₃CHMe— | | Me | O | OCHF₂ | Cl |
| 9-13 | F | Br | H | —(CH₂)₅— | | Me | O | OCHF₂ | Cl |
| 9-14 | H | Cl | H | Ph | H | Me | S | OCHF₂ | Cl |
| 9-15 | Cl | Cl | H | 2-pyridyl | Me | Me | O | OCHF₂ | Cl |
| 9-16 | F | Cl | H | 2-pyrimidyl | Et | Me | NH | OCHF₂ | Cl |
| 9-17 | F | Cl | H | t-Bu | t-Bu | Me | O | OCHF₂ | Cl |
| 9-18 | F | Cl | H | H | C(O)OEt | Me | O | OCHF₂ | Cl |
| 9-19 | F | Cl | H | H | C(O)OtBu | Me | O | OCHF₂ | Cl |
| 9-20 | H | Cl | H | H | Ac | Me | O | OCHF₂ | Cl |
| 9-21 | H | CF₃ | H | Me | Me | Me | O | OCHF₂ | Cl |
| 9-22 | F | MeO | H | —C(O)(CH₂)₃— | | Me | S | OCHF₂ | Cl |
| 9-23 | F | Cl | H | Bn | Bn | Me | O | OCHF₂ | Cl |

TABLE 10

| Compd. No. | X | Y | R2 | R3 | R4 | R7 | A | A1 | R8 |
|---|---|---|---|---|---|---|---|---|---|
| 10-1 | H | Cl | H | Me | Me | Me | O | O | Me |
| 10-2 | H | Cl | H | Ph | Ac | Me | O | O | Me |
| 10-3 | F | Cl | Me | Me | Me | Me | O | S | Me |
| 10-4 | F | Cl | Me | Me | Me | Me | O | O | NH2 |
| 10-5 | F | Cl | Me | Me | Me | Me | O | O | Me |
| 10-6 | F | Cl | Me | Me | Me | Bn | O | O | Me |
| 10-7 | F | Cl | Me | Me | Propargyl | Me | O | O | Me |
| 10-8 | F | Cl | H | Ph | Benzyl | Me | O | O | Me |
| 10-9 | F | Cl | Me | Ph | Allyl | Me | O | O | Me |
| 10-10 | F | Cl | Et | Et | Me | Allyl | O | O | Me |
| 10-11 | F | Br | —(CH2)4— | | Me | Me | O | O | Me |
| 10-12 | F | Cl | —CHMe(CH2)3CHMe— | | CHF2 | Me | O | O | Me |
| 10-13 | F | Br | —(CH2)5— | | Me | Me | O | O | Me |
| 10-14 | H | Cl | Ph | H | Me | Me | S | O | Me |
| 10-15 | Cl | Cl | 2-pyridyl | Me | Me | Me | O | O | Me |
| 10-16 | F | Cl | 2-pyrimidyl | Et | Me | Me | NH | O | Me |
| 10-17 | F | Cl | t-Bu | t-Bu | Me | Me | O | O | Me |
| 10-18 | F | Cl | H | C(O)OEt | Me | Me | O | O | Me |
| 10-19 | F | Cl | H | C(O)OtBu | 2-Chlorobenzyl | Me | O | O | Me |
| 10-20 | H | Cl | H | Ac | Me | Me | O | O | Me |
| 10-21 | H | CF3 | Me | Me | Me | Me | O | O | Me |
| 10-22 | F | MeO | —C(O)(CH2)3— | | Me | Me | S | O | Me |
| 10-23 | F | Cl | Bn | Bn | Me | Me | O | O | Me |

TABLE 11

| Compd. No. | X | Y | R2 | R3 | R4 | R7 | A | R13 | R10 |
|---|---|---|---|---|---|---|---|---|---|
| 11-1 | H | Cl | H | Me | Me | Me | O | OCHF2 | Cl |
| 11-2 | H | Cl | H | Ph | Ac | Me | O | OCHF2 | Cl |
| 11-3 | F | Cl | Me | Me | Me | Me | O | OCHF2 | Cl |
| 11-4 | F | Cl | Me | Me | Me | Me | O | SCHF2 | Cl |
| 11-5 | F | Cl | Me | Me | Me | Me | O | OCHF2 | CN |
| 11-6 | F | Cl | Me | Me | Me | Bn | O | OCHF2 | Cl |
| 11-7 | F | Cl | Me | Me | Propargyl | Me | O | OCHF2 | Cl |
| 11-8 | F | Cl | H | Ph | Benzyl | Me | O | OCHF2 | Cl |
| 11-9 | F | Cl | Me | Ph | Allyl | Me | O | OCHF2 | Cl |
| 11-10 | F | Cl | Et | Et | Me | Allyl | O | OCHF2 | Cl |
| 11-11 | F | Br | —(CH2)4— | | Me | Me | O | OCHF2 | Cl |
| 11-12 | F | Cl | —CHMe(CH2)3CHMe— | | CHF2 | Me | O | OCHF2 | Cl |
| 11-13 | F | Br | —(CH2)5— | | Me | Me | O | OCHF2 | Cl |
| 11-14 | H | Cl | Ph | H | Me | Me | S | OCHF2 | Cl |
| 11-15 | Cl | Cl | 2-pyridyl | Me | Me | Me | O | OCHF2 | Cl |
| 11-16 | F | Cl | 2-pyrimidyl | Et | Me | Me | NH | OCHF2 | Cl |
| 11-17 | F | Cl | t-Bu | t-Bu | Me | Me | O | OCHF2 | Cl |
| 11-18 | F | Cl | H | C(O)OEt | Me | Me | O | OCHF2 | Cl |
| 11-19 | F | Cl | H | C(O)OtBu | 2-Chlorobenzyl | Me | O | OCHF2 | Cl |
| 11-20 | H | Cl | H | Ac | Me | Me | O | OCHF2 | Cl |
| 11-21 | H | CF3 | Me | Me | Me | Me | O | OCHF2 | Cl |
| 11-22 | F | MeO | —C(O)(CH2)3— | | Me | Me | S | OCHF2 | Cl |

TABLE 11-continued

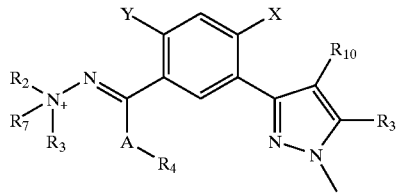

| Compd. No. | X | Y | $R_2$ | $R_3$ | $R_4$ | $R_7$ | A | $R_{13}$ | $R_{10}$ |
|---|---|---|---|---|---|---|---|---|---|
| 11-23 | F | Cl | Bn | Bn | Me | Me | O | $OCHF_2$ | Cl |

Note:
Me; methyl group
Et; ethyl group
t-Bu; t-butyl group
Ph; phenyl group
Bn; benzyl group
Ac; acetyl group Table 12 lists the NMR data for some representative compounds of this invention.

TABLE 12

| Compd. No. | $^1$H-NMR(300 MHz,ppm) |
|---|---|
| 1-4 | CDCl$_3$, 2.76(6H, s), 3.54(3H, br s), 6.35(1H, s), 7.23(1H, dd, J = 8.5, 2.6 Hz), 7.50(1H, d, J = 2.5 Hz), 7.53(1H, d, J = 8.5 Hz). |
| 1-9 | CDCl$_3$, 3.29(3H, s), 3.56(3H, br s), 6.37(1H, s), 6.87–6.95 (5H, m), 7.38(1H, d, J = 9.0 Hz), 7.72(1H, d, J = 7.6 Hz), 8.05(1H, br s). |
| 1-11 | CDCl$_3$, 1.82(4H, m), 3.21(4H, m), 3.55(3H, br s), 6.34(3H, s), 7.2–7.3(2H, m). |
| 1-14 | DMSO-d$_6$, 2.03–2.80(8H, m), 3.32(3H, s), 3.79(3H, s), 6.96(0.6H, s), 6.98(0.4H, s), 7.40(0.4H, d, J = 7.7 Hz), 7.49(0.6H, d, J = 7.7 Hz), 7.69(0.4H, d, J = 9.7 Hz), 7.75(0.6H, d, J = 9.7 Hz), 9.30(0.4H, br s), 9.56 (0.6H, br s). |
| 1-15 | DMSO-d$_6$, 0.97–1.80(8H, m), 1.05(3H, s), 1.07(3H, s), 3.79(3H, s), 6.96(1H, s), 7.48(1H, d, J = 7.7 Hz), 7.75(1H, d, J = 9.7 Hz), 9.05(1H, br s). |
| 1-16 | DMSO-d$_6$, 0.90–1.80(8H, m), 1.06(3H, s), 1.08(3H, s), 3.40 (3H, s), 6.59(1H, s), 7.55(1H, d, J = 7.7 Hz), 7.77(1H, d, J = 9.7 Hz), 9.10(1H, br s). |
| 1-23 | CDCl$_3$, 1.28(3H, t, J = 7.1 Hz), 3.50(3H, br s), 4.19(2H, q, J = 7.1 Hz), 6.31(1H, s), 7.01(1H, br s), 7.35(1H, d, J = 9.0 Hz), 7.65(1H, d, J = 7.5 Hz), 8.55(1H, br s). |
| 1-24 | CDCl$_3$, 1.48(9H, s), 3.52(3H, br s), 6.33(1H, s), 6.77(1H, hr s), 7.35(1H, d, J = 9.0 Hz), 7.69(1H, d, J = 7.5 Hz), 8.29(1H, br s). |
| 1-29 | Aceton-d$_6$, 3.51(2.2H, in), 3.62(0.8H, in), 4.23(0.8H, s), 6.01 (0.3H, d, J = 7.7 Hz), 6.39(0.7H, s), 6.54(0.3H, s), 7.1–7.51 (10.7H, m) 7.40(0.7H, d, J = 9.6 Hz), 7.43(0.3H, d, J = 9.6 Hz), 8.30(0.3H, hr s), 8.80(0.7H, br s). |
| 4-4 | CDCl$_3$, 2.48(3H, s), 2.82(6H, s), 3.54(3H, br s), 6.36(1H, s), 7.14(1H, d, J = 2.3 Hz), 7.18(1H, dd, J = 2.3, 8.4 Hz), 7.49 (1H, d, J = 8.5 Hz). |
| 4-8 | CDCl$_3$, 0.90–1.80(12H, m), 3.54(3H, br s), 3.80(2H, m), 6.34 (1H, s), 7.14(1H, d, J = 7.2 Hz), 7.26(1H, s), 7.35(1H, d, J = 9.2 Hz). |
| 4-9 | CDCl$_3$, 0.90–1.80(12H, m), 2.36(3H, s), 3.54(3H, br s), 3.80 (2H, m), 6.34(1H, s), 7.05(1H, d, J = 7.2 Hz), 7.29(1H, d, J = 9.2 Hz). |
| 5-2 | CDCl$_3$, 1.07(9H, s), 1.81(3H, s), 2.53(3H, s), 3.54(3H, br s), 6.34(1H, s), 7.24(1H, d, J = 7.3 Hz), 7.29(1H, d, J = 9.2 Hz). |
| 5-3 | CDCl$_3$, 1.05(9H, s), 2.04(3H, s), 3.40(3H, s), 3.54(3H, br s), 6.34(1H, s), 7.21(1H, d, J = 7.2 Hz), 7.32(1H, d, J = 9.2 Hz). |
| 5-4 | CDCl$_3$, 1.13(9H, s), 1.89(3H, s), 3.59(3H, br s), 6.34(1H, s), 7.00 (1H, s), 7.27(1H, d, J = 7.3 Hz), 7.32(1H, d, J = 9.2 Hz). |
| 5-6 | CDCl$_3$, 1.06(9H, s), 1.43(9H, s), 3.53(3H, m), 3.98(3H, s), 6.33 (1H, s), 7.17(1H, d, J = 7.6 Hz), 7.29(1H, d, J = 9.3 Hz). |

TABLE 12-continued

| Compd. No. | $^1$H-NMR(300 MHz,ppm) |
|---|---|
| 5-7 | CDCl$_3$, 1.07(9H, s), 1.43(9H, s), 2.50(1H, t, J = 2.4 Hz), 3.54 (3H, m), 4.96(2H, d, J = 2.4 Hz), 6.33(1H, s), 7.20(1H, d, J = 7.6 Hz), 7.30(1H, d, J = 9.3 Hz). |
| 6-4 | CDCl$_3$, 1.02(6H, s), 1.40(6H, s), 1.42(3H, s), 1.52(3H, s), 3.59 (3H, m), 6.33(0.7H, s), 6.36(0.3H, s), 7.28(0.7H, d, J = 9.2 Hz), 7.33(0.7H, d, J = 7.5 Hz), 7.34(0.3H, d, J = 10.0 Hz), 7.82 (0.3H, d, J = 7.9 Hz), 9.07(1H, br s). |
| 6-5 | CDCl$_3$, 0.98(4.2H, s), 1.45(0.8H, s), 1.22(4.0H, s), 1.83 (1.6 H, s), 1.91(1.15H, s), 2.14(0.25 H, s), 3.55(3H, m), 6.34 (1H, m), 7.25–7.37(1.6H, m), 7.78(0.4H, d, J = 7.7 Hz), 9.01 (0.4H, bs). |
| 6-8 | CDCl$_3$, 1.10(4.5H, s), 1.31(4.5H, s), 1.37(4.5H, s), 1.40 (4.5H, s), 3.02(1.5H, s), 3.25(1.5H, s), 3.52(1.5H, m), 3.55 (1.5H, m), 6.32(0.5H, s), 6.35(0.5H, s), 7.22(0.5H, d, J = 7.5 Hz), 7.26(1H, m), 7.34(0.5H, Hz, 9.2 Hz). |
| 6-15 | CDCl$_3$, 3.56(3H, m), 6.36(0.5H, s), 6.37(0.5H, s), 7.1–7.9 (12H, m), 8.70(0.5H, br s), 9.41(0.5H, br s) |

Herbicidal Activity

The compounds of the present invention exhibit excellent herbicidal effects when used as an active ingredient of a herbicide. The herbicide can be used for a wide range of applications, for example on crop lands such as paddy fields, upland farms, orchards and mulberry fields, and non-crop lands such as forests, farm roads, playgrounds, and factory sites. The application method may be suitably selected for soil treatment application and foliar application.

The compounds of the present invention are capable of controlling noxious weeds including grass (gramineae) such as barnyardgrass (*Echinochloa crus-galli*), large crabgrass (*Digitaria sanguinalis*), green foxtail (*Setaria viridis*), goosegrass (*Eleusine indica* L.), wild oat (Avenafatua L.), Johnsongrass (*Sorghum halepense*), quackgrass (*Agropyron repens*), alexandergrass (*Brachiaria plantaginea*), paragrass (*Panicum purpurascen*), sprangletop (*Leptochloa chinensis*) and red sprangletop (*Leptochloa panicea*); sedges (or Cyperaceae) such as rice flatsedge (*Cyperus iria* L.), purple nutsedge (*Cyperus rotundus* L.), Japanese bulrush (*Scirpus Juncoides*), flatsedge (*Cyperus serotinus*), small-flower umbrellaplant (*Cyperus difformis*), slender spikerush (*Eleocharis acicularis*), and water chestnut (*Eleocharis kuroguwai*); alismataceae such as Japanese ribbon wapato (*Sagittaria pygmaea*), arrow-head (*Sagittaria trifolia*) and narrowleaf waterplantain (*Alisma canaliculatum*); pontederiaceae such as monochoria (*Monochoria vaginalis*) and monochoria species (*Monochoria korsakowii*); scrophulariaceae such as false pimpernel (*Lindernia pyxidaria*) and abunome (*Dopatrium Junceum*); lythraceae such as toothcup (*Rotala indica*) and red stem (*Ammannia multiflora*); and broadleaves such as redroot pigweed (*Amaranthus retroflexus*), velvetleaf (*Abutilon theophrasti*), momingglory (*Ipomoea hederacea*), lambsquarters (*Chenopodium album*), prickly sida (*Sida spinosa* L.), common purslane (*Portulaca oleracea* L.), slender amaranth (*Amaranthus viridis* L.), sicklepod (*Cassia obtusifolia*), black nightshade (*Solanum nigrum* L.), pale smartweed (*Polygonum lapathifolium* L.), common chickweed (*Stellaria media* L.), common cocklebur (*Xanthium strumarium* L.), flexuous bittercress (*Cardamine flexuosa* WITH.), henbit (*Lamium amplexicaule* L.) and threeseeded copperleaf (*Acalypha australis* L.). Accordingly, it is useful for controlling noxious weeds non-selectively or selectively in the cultivation of a crop plant such as corn (*Zea mays* L.), soybean (*Glycine max* Merr.), cotton (Gossypium spp.), wheat (Triticum spp.), rice (*Oryza sativa* L.), barley (*Hordeum vulgare* L.), oat (*Avena sativa* L.), sorgo (*Sorghum bicolor* Moench), rape (*Brassica napus* L.), sunflower (*Helianthus annuus* L.), sugar beet (*Beta vulgaris* L.), sugar cane (*Saccharum officinarum* L.), Japanese lawngrass (*Zoysia Japonica* stend), peanut (*Arachis hypogaea* L.) or flax (*Linum usitatissimum* L.).

For use as herbicides, the active ingredients of this invention are formulated into herbicidal compositions by mixing herbicidally active amounts with inert ingredients known to the art to facilitate either the suspension, dissolution or emulsification of the active ingredient for the desired use. The type of formulation prepared recognizes the facts that formulation, crop and use pattern all can influence the activity and utility of the active ingredient in a particular use. Thus for agricultural use the present herbicidal compounds may be formulated as water dispersible granules, granules for direct application to soils, water soluble concentrates, wettable powders, dusts, solutions, emulsifiable concentrates (EC), microemulsion, suspoemulsion, invert emulsion or other types of formulations, depending on the desired weed targets, crops and application methods.

These herbicidal formulations may be applied to the target area (where suppression of unwanted vegetation is the objective) as dusts, granules or water or solvent diluted sprays. These formulation may contain as little as 0.1% to as much as 97% active ingredient by weight.

Dusts are admixtures of the active ingredient with finely ground materials such as clays (some examples include kaolin and montmorillonite clays), talc, granite dust or other organic or inorganic solids which act as dispersants and carriers for the active ingredient; these finely ground materials have an average particle size of less than 50 microns. A typical dust formulation will contain 1% active ingredient and 99% carrier.

Wettable powders are composed of finely ground particles which disperse rapidly in water or other spray carriers. Typical carriers include kaolin clays, Fullers earth, silicas and other absorbent, wettable inorganic materials. Wettable powders can be prepared to contain from 1 to 90% active ingredient, depending on the desired use pattern and the absorbability of the carrier. Wettable powders typically contain wetting or dispersing agents to assist dispersion in water or other carriers.

Water dispersible granules are granulated solids that freely disperse when mixed in water. This formulation typically consists of the active ingredient (0.1% to 95% active ingredient), a wetting agent (1–15% by weight), a dispersing agent (1 to 15% by weight) and an inert carrier (1–95% by weight). Water dispersible granules can be formed by mixing the ingredients intimately then adding a small amount of water on a rotating disc (said mechanism is commercially available) and collecting the agglomerated granules. Alternatively, the mixture of ingredients may be mixed with an optimal amount of liquid (water or other liquid) and passed through an extruder (said mechanism is commercially available) equipped with passages which allow for the formation of small extruded granules. Alternatively, the mixture of ingredients can be granulated using a high speed mixer (said mechanism is commercially available) by adding a small amount of liquid and mixing at high speeds to affect agglomeration. Alternatively, the mixture of ingredients can be dispersed in water and dried by spraying the dispersion through a heated nozzle in a process known as spray drying (spray drying equipment is commercially available). After granulation the moisture content of granules is adjusted to an optimal level (generally less than 5%) and the product is sized to the desired mesh size.

Granules are granulated solids that do not disperse readily in water, but instead maintain their physical structure when applied to the soil using a dry granule applicator. These granulated solids may be made of clay, vegetable material such as corn cob grits, agglomerated silicas or other agglomerated organic or inorganic materials or compounds such as calcium sulfate. The formulation typically consists of the active ingredient (1 to 20%) dispersed on or absorbed into the granule. The granule may be produced by intimately mixing the active ingredient with the granules with or without a sticking agent to facilitate adhesion of the active ingredient to the granule surface, or by dissolving the active ingredient in a solvent, spraying the dissolved active ingredient and solvent onto the granule then drying to remove the solvent. Granular formulations are useful where in-furrow or banded application is desired.

Emulsifiable concentrates (EC) are homogeneous liquids composed of a solvent or mixture of solvents such as xylenes, heavy aromatic naphthas, isophorone or other proprietary commercial compositions derived from petroleum distillates, the active ingredient and an emulsifying agent or agents. For herbicidal use, the EC is added to water (or other spray carrier) and applied as a spray to the target area. The composition of an EC formulation can contain 0.1% to 95% active ingredient, 5 to 95% solvent or solvent mixture and 1 to 20% emulsifying agent or mixture of emulsifying agents.

Suspension concentrate (also known as flowable) formulations are liquid formulations consisting of a finely ground suspension of the active ingredient in a carrier, typically water or a non-aqueous carrier such as an oil. Suspension concentrates typically contain the active ingredient (5 to 50% by weight), carrier, wetting agent, dispersing agent, anti-freeze, viscosity modifiers and pH modifiers. For application, suspension concentrates are typically diluted with water and sprayed on the target area.

Solution concentrates are solutions of the active ingredient (1 to 70%) in solvents which have sufficient solvency to dissolve the desired amount of active ingredient. Because they are simple solutions without other inert ingredients such as wetting agents, additional additives are usually added to the spray tank mix before spraying to facilitate proper application.

Microemulsions are solutions consisting of the active ingredient (1 to 30%) dissolved in a surfactant or emulsifier, without any additional solvents. There are no additional solvents added to this formulation. Microemulsions are particularly useful when a low odor formulation is required such as in residential turfgrass applications.

Suspoemulsions are combinations of two active ingredients. One active ingredient is made as a suspension concentrate (1–50% active ingredient) and the second active is made as an emulsifiable concentrate (0.1 to 20%). A reason for making this kind of formulation is the inability to make an EC formulation of the first ingredient due to poor solubility in organic solvents. The suspoemulsion formulation allows for the combination of the two active ingredients to be packaged in one container, thereby minimizing packaging waste and giving greater convenience to the product user.

The herbicidal compounds of this invention may be formulated or applied with insecticides, fungicides, acaricides, nematicides, fertilizers, plant growth regulators or other agricultural chemicals. Certain tank mix additives, such as spreader stickers, penetration aids, wetting agents, surfactants, emulsifiers, humectants and UV protectants may be added in amounts of 0.01% to 5% to enhance the biological activity, stability, wetting, spreading on foliage or uptake of the active ingredients on the target area or to improve the suspensibility, dispersion, redispersion, emulsifiability, UV stability or other physical or physicochemical property of the active ingredient in the spray tank, spray system or target area.

The compositions of the present invention may be used in admixture with or in combination with other agricultural chemicals, fertilizers or phytotoxicity-reducing agents. In such a case, they may exhibit even better effects or activities. As other agricultural chemicals, herbicides, fungicides, antibiotics, plant hormones, insecticides, or acaricides may, for example, be mentioned. Especially with herbicidal compositions having the compounds of the present invention used in admixture with or in combination with one or more active ingredients of other herbicides, it is possible to improve the herbicidal activities, the range of application time(s) and the range of applicable weed types. Further, the compounds of the present invention and an active ingredient of another herbicide may be separately formulated so they may be mixed for use at the time of application, or both may be formulated together. The present invention covers such herbicidal compositions.

The blend ratio of the compounds of the present invention with the active ingredient of other herbicides can not generally be defined, since it varies depending on the time and method of application, weather conditions, soil type and type of formulation. However one active ingredient of other herbicide may be incorporated usually in an amount of 0.01 to 100 parts by weight, per one part by weight of the compounds of the present invention. Further, the total dose of all of the active ingredients is usually from 1 to 10000 g/ha, preferably from 5 to 500 g/ha. The present invention covers such herbicidal compositions.

As the active ingredients of other herbicides, the following (common name) may be mentioned. Herbicidal compositions having the compounds of the present invention used in combination with other herbicides, may occasionally exhibit a synergistic effect.

1. Those that are believed to exhibit herbicidal effects by disturbing auxin activities of plants, including a phenoxy acetic acid type such as 2,4-D, 2,4-DB, 2,4-DP, MCPA, MCPP, MCPB or naproanilide (including the free acids, esters or salts thereof), an aromatic carboxylic type such as 2, 3, 6 TBA, dicamba, dichlobenil, a pyridine type such as picloram (including free acids and salts thereof), triclopyr or clopyralid and others such as naptalam, benazolin or quinclorac.

2. Those that are believed to exhibit herbicidal effects by inhibiting photosynthesis of plants including a urea type such as diuron, linuron, isoproturon, chlorotoluron, metobenzuron, tebuthiuron or fluometuron, a triazine type such as simazine, atrazine, cyanazine, propazine, terbuthylazine, atraton, hexazinone, metribuzin, metamitron, simetryn, triazaflam, terbutryn, ametryn, prometryn or dimethametryn, a uracil type such as bromacil, terbacil or lenacil, an anilide type such as propanil or cypromid, a carbamate type such as desmedipham or phenmedipham, a hydroxybenzonitrile type such as bromoxynil or ioxynil, and others such as pyridate, bentazon and methazole.

3. A quaternary ammonium salt type such as paraquat, diquat or difenzoquat, which is believed to be converted to free radicals by itself to form active oxygen in the plant and thus to exhibit quick herbicidal effects.

4. Those which are believed to exhibit herbicidal effects by inhibiting chlorophyll biosynthesis in plants and abnormally accumulating a photosensitizing peroxide substance in the plant body, including a diphenyl ether type such as nitrofen, lactofen, acifluorfen-sodium, oxyfluorfen, fomesafen, bifenox, or chlomethoxyfen, a cyclic amide type such as chlorphthalim, flumioxadine, flumiclorac-pentyl, flumioxazine, or cinidon-ethyl, and others such as fluthiacetmethyl, pyraflufen-ethyl, pentoxazone, azafenidin, oxadiargyl, oxadiazon, carfentrazone, sulfentrazone, fluazolate, butafenacil, or thidiazimin.

5. Those which are believed to exhibit herbicidal effects characterized by whitening activities by inhibiting chromogenesis of plants such as carotenoids including a pyridazinone type such as norflurazon, chloridazon or metflurazon, a pyrazol type such as pyrazolate, pyrazoxyfen or benzofenap, and others such as fluridone, fluramone, diflufenican, methoxyphenone, clomazone, amitrole, sulcotrione, mesotrione, isoxaflutole and isoxachlortole.

6. Those which exhibit herbicidal effects specifically to gramineous plants including an aryloxyphenoxypropionic acid type such as diclofop-methyl, pyrofenop-sodium, fluazifop-butyl, haloxyfop-methyl, quizalofop-ethyl, fenoxaprop ethyl, or cyhalofop-butyl and a cyclohexanedione type such as alloxydim-sodium, sethoxydim, clethodim, tepraloxydim, clefoxydim butroxydim, or tralkoxydim.

7. Those which are believed to exhibit herbicidal effects by inhibiting amino acid biosynthesis of plants, including a sulfonylurea type such as chlorimuron-ethyl, nicosulfuron, metsulfuron-methyl, triasulfuron, primisulfuron, tribenuron-methyl, chlorosulfuron, bensulfuron-methyl, sulfometuron-methyl, prosulfuron, halosulfuron-methyl, thifensulfuron-methyl, triflusulfuron-methyl, rimsulfuron, azimsulfuron, flazasulfuron, imazosulfuron, cyclosulfamuron, oxasulfuron, flupyrsulfuron, sulfosulfuron, amidosulfuron, ethyoxysulfuron, foramsulfuron, iodosulfuron, cinosulfuron, a triazolopyrimidinesulfonamide type such as chlorasulam-methyl, flumetsulam, diclosulam, florasulam or metosulam, an imidazolinone type such as imazapyr, imazethapyr, imazaquin, imazamox, imazapic, imazameth, imazamethabenz methyl, a pyrimidinesalicylic acid type such as pyrithiobac--sodium, bisyribac-sodium or pyriminobac-methyl, and others such as glyphosate, and its' salts such as glyphosate-ammonium, glyphosate-isopropylamine or sulfosate.

8. Those which are believed to exhibit herbicidal effects by interfering with the normal metabolism of inorganic nitrogen assimilation such as glufosinate, glufosinate-ammonium, phosphinothricin or bialophos.

9. Those which are believed to exhibit herbicidal effects by inhibiting cell division of plant cells, including a dinitroaniline type such as trifluralin, oryzalin, nitralin, pendamethalin, ethafluralin, benefin and prodiamine, an amide type such as bensulide, napronamide, and pronamide, a carbamate type such as propham, chlorpropham, barban, and asulam, an organophosphorous type such as amiprofos-methyl or butamifos, an oxyacetamide type such as mefenacet or flufenacet, a carboxamide type such as fentrazamide or cafenstrole and others such as DCPA, thiazopyr and dithiopyr.

10. Those which are believed to exhibit herbicidal effects by inhibiting protein synthesis or long chain fatty acid synthesis of plant cells, including a chloroacetanilide type such as alachlor, metolachor, propachlor, butachlor, pretilachlor, thenylchlor, propisochlor, betenachlor, acetochlor (including combinations with herbicide safeners) and dimethenamid.

11. Those in which the mode of action causing the herbicidal effects are not well understood including the dithiocarbamates such as thiobencarb, pyributacarb, EPTC, diallate, triallate, molinate, dimepiperate, pebulate, cycloate, butylate, vernolate or prosulfocarb and miscellaneous herbicides such as MSMA, DSMA, endothall, ethofumesate, sodium chloride, pelargonic acid, indanofan, fosamine, cafenstrole, amicarbazone, propoxycarbazone, flucarbazone, isoxaben, quinchlorac, quinmerac, cinmethylin, diflufenzopyr-sodium, napropamide A few formulation examples of the present invention are given as follows.

Formulation example 1. Emulsifiable Concentrate

| Ingredient Trade Name | Chemical Name | Supplier | Function | % wt./wt. |
|---|---|---|---|---|
| Compound 1-9 | | | Active Ingredient | 5.0 |
| Toximul H-A | Calcium sulfonate and nonionic surfactant blend | Stepan Co. | Emulsifier | 2.5 |
| Toximul D-A | Calcium sulfonate and nonionic surfactant blend | Stepan Co. | Emulsifier | 7.5 |
| Aromatic 200 | Aromatic hydrocarbon | Exxon Chemical Co. | Solvent | QS to 100% |

Formulation example 2. Suspension Concentrate

| Ingredient Trade Name | Chemical Name | Supplier | Function | % wt./wt. |
|---|---|---|---|---|
| Compound 1-15 | | | Active Ingredient | 10.00 |
| Proylene gylcol | | | Anti-freeze | 5.00 |
| Antifoam 1530 | Silicone defoamer | Dow Corning | Anti-foam | 0.50 |
| Rhodopol 23 | Xanthan gum | Rhone-Poulenc | Suspending Aid | 0.25 |
| Morwet D-425 | Napthalene formaldehyde condensate | Witco Corp. | Dispersant | 3.00 |
| Igepal CA-720 | Octylphenol ethoxylate | Rhone-Poulenc | Welling agent | 3.00 |
| Proxel GXL | 1,2 benziso-thiazolin-3-one | ICI Americas | Preservative | 0.25 |
| Water | | | Diluent | 68.00 |

Formulation example 3. Wettable Powder

| Ingredient Trade Name | Chemical Name | Supplier | Function | % wt./wt. |
|---|---|---|---|---|
| Compound 1-29 | | | Active Ingredient | 50.00 |
| Geropon T-77 | Sodium-N-methyl-N-oleoyl taurate | Rhone-Poulenc | Wetting agent | 3.00 |
| Lomar PW | Napthalene Sulfonate | Henkel Corp. | Dispersant | 5.00 |
| Kaolin clay | Kaolin clay | J. M. Huber | Filler | 42.00 |

Formulation example 4. Water Dispersible Granule

| Ingredient Trade Name | Chemical Name | Supplier | Function | % wt./wt. |
|---|---|---|---|---|
| Compound 4-9 or 6-4 | | | Active Ingredient | 50.00 |
| Morwet EFW | | Witco Corp. | Wetting agent | 2.00 |
| Morwet D-425 | Napthalene formaldehyde condensate | Witco Corp. | Dispersant | 10.00 |
| ASP 400 | Kaolin Clay | Engelhard Corp. | Filler | 38.00 |

Test Example

A standard greenhouse herbicide activity screening system was used to evaluate the herbicidal efficacy and crop safety of these test compounds. Seven broadleaf weed species including redroot pigweed (*Amaranthus retroflexus*, AMARE), velvetleaf (*Abutilon theophrasti*, ABUTH), sicklepod (*Cassia obtusifolia*, CASOB), ivyleaf morningglory (*Ipomoea hederacea*, IPOHE), lambsquarters (*Chenopodium album*, CHEAL), common ragweed (*Ambrosia artemisiifolia* L., AMBEL), and cocklebur (*Xanthium strumarium*, XANST) were used as test species. Four grass weed species including green foxtail (*Setaria viridis*, SETVI), barnyardgrass (*Echinochloa crus-galli*, ECHCG), johnsongrass (*Sorghum halepense*, SORHA), and large crabgrass (*Digitaria sanguinalis*, DIGSA) were also used. In addition, four crop species, field corn (*Zea mays* L., var. Dekalb 535, CORN), soybean (*Glycine max* L., var. Pella 86, SOY), upland rice (*Oryza* sp., var.Cocodrie, RICE) and wheat (*Triticum aestivum* L.) were included.

All plants were grown in 10 cm square plastic pots which were filled with a sandy loam soil mix. For pre-emerge tests, seeds were planted one day prior to application of the test compounds. For post-emerge tests, seeds were planted 8–21 days prior to the test to allow emergence and good foliage development prior to application of the test substances. At the time of the post-emerge application, plants of all species were usually at the 2–3 leaf stage of development.

All test compounds were dissolved in acetone and applied to the test units in a volume of 187 l/ha. Test materials were applied at rates ranging from 15 g ai/ha to 1000 g ai/ha using a track sprayer equipped with a TJ8001E even flow flat fan spray nozzle. Plants were arranged on a shelf so that the top of the canopy (post-emerge) or top of the soil surface (pre-emerge) was 40–45 cm below the nozzle. Pressurized air was used to force the test solution through the nozzle as it was mechanically advanced (via electrically driven chain drive) over the top of all test plants/pots. This application simulates a typical commercial field herbicide application. Pre-emergence tests were top watered immediately after treatment to incorporate the test materials, then routinely top-watered for normal growth. Post-emerge test units were always bottom-watered.

At 14 days after application of the test materials, phytotoxicity ratings were recorded. A rating scale of 0–100 was used as previously described in *Research Methods in Weed Science,* 2nd edition, B. Truelove, Ed., Southern Weed Science Society, Auburn University, Auburn, Ala., 1977. Briefly, "0" corresponds to no damage and "100" corresponds to complete death of all plants in the test unit. This scale was used both to determine efficacy against weed species and damage to crop species. Herbicide activity data for various compounds of this invention, which are shown by compound No. in Tables 1–12, are shown in Tables 13 and 14. The data demonstrate significant differences between compounds for both efficacy against weeds and selectivity for crop species. For selected compounds, excellent activity against a majority of the weed species was observed with minimal damage to at least one of the crop species.

TABLE 13

Herbicidal Activity of compounds in Table 12 when applied POST emergent at 63 and 250 ga.i./ha.

| Cmpd. no. | Rate g ai/ha | AMARE | ABUTH | CASOB | IPOHE | CHEAL | AMBEL | XANST | SETVI | ECHCO | SORHA |
|---|---|---|---|---|---|---|---|---|---|---|---|
| 1-4 | 63 | 100 | 100 | 70 | 100 | 99 | 80 | 100 | 65 | 65 | 50 |
| | 250 | 100 | 100 | 80 | 100 | 100 | 100 | 100 | 75 | 95 | 80 |
| 1-9 | 63 | 100 | 100 | 80 | 100 | 100 | 99 | 100 | 60 | 98 | 75 |
| | 250 | 100 | 100 | 95 | 100 | 100 | 100 | 100 | 95 | 100 | 99 |
| 1-11 | 63 | 100 | 100 | 15 | 100 | 90 | 99 | 75 | 50 | 70 | 70 |
| | 250 | 100 | 100 | 80 | 100 | 100 | 100 | 100 | 55 | 100 | 80 |
| 1-14 | 63 | 0 | 0 | 0 | 100 | 0 | 0 | 70 | 0 | 0 | 0 |
| | 250 | 30 | 35 | 0 | 100 | 70 | 50 | 70 | 0 | 0 | 0 |
| 1-15 | 63 | 90 | 100 | 70 | 75 | 98 | 80 | 100 | 20 | 50 | 0 |
| | 250 | 100 | 100 | 75 | 100 | 100 | 95 | 100 | 55 | 80 | 30 |
| 1-16 | 63 | 100 | 100 | 98 | 100 | 100 | 99 | 75 | 90 | 35 | 75 |
| | 250 | 100 | 100 | 99 | 100 | 100 | 99 | 100 | 99 | 98 | 99 |
| 1-23 | 63 | 100 | 100 | 98 | 98 | 100 | 85 | 100 | 55 | 50 | 70 |
| | 250 | 100 | 100 | 98 | 100 | 100 | 100 | 100 | 99 | 75 | 99 |
| 1-24 | 63 | 100 | 100 | 75 | 100 | 100 | 100 | 100 | 35 | 35 | 35 |
| | 250 | 100 | 100 | 95 | 100 | 100 | 100 | 100 | 60 | 50 | 55 |
| 1-29 | 63 | 100 | 100 | 50 | 90 | 100 | 75 | 0 | 99 | 55 | 99 |
| | 250 | 100 | 100 | 100 | 100 | 100 | 100 | 90 | 100 | 100 | 100 |
| 4-4 | 63 | 100 | 100 | 65 | 100 | 100 | 75 | 0 | 50 | 30 | 60 |
| | 250 | 100 | 100 | 98 | 100 | 100 | 100 | 60 | 90 | 90 | 90 |
| 4-8 | 63 | 100 | 100 | 70 | 100 | 100 | 80 | 100 | 15 | 70 | 10 |
| | 250 | 100 | 100 | 75 | 100 | 100 | 100 | 100 | 60 | 90 | 65 |
| 4-9 | 63 | 100 | 100 | 60 | 95 | 100 | 60 | 30 | 65 | 0 | 0 |
| | 250 | 100 | 100 | 90 | 100 | 100 | 99 | 60 | 100 | 15 | 80 |
| 5-2 | 63 | 95 | 100 | 55 | 100 | 100 | 90 | 99 | 50 | 95 | 55 |
| | — | — | — | — | — | — | — | — | — | — | — |
| 5-3 | 63 | 99 | 95 | 50 | 100 | 80 | 90 | 70 | 60 | 100 | 30 |
| | 250 | — | — | — | — | — | — | — | — | — | — |
| 5-4 | 63 | 95 | 99 | 50 | 100 | 70 | 95 | 65 | 55 | 90 | 30 |
| | 250 | — | — | — | — | — | — | — | — | — | — |
| 5-6 | 63 | 100 | 75 | 40 | 35 | 100 | 35 | 0 | 95 | 40 | 25 |
| | 250 | 100 | 95 | 98 | 70 | 100 | 99 | 10 | 100 | 90 | 100 |
| 5-7 | 63 | 70 | 30 | 50 | 60 | 70 | 50 | 0 | 50 | 35 | 0 |
| | 250 | 99 | 70 | 50 | 70 | 85 | 55 | 55 | 55 | 55 | 15 |
| 6-4 | 63 | 100 | 100 | 99 | 100 | 100 | 75 | 100 | 85 | 80 | 75 |
| | 250 | 100 | 100 | 95 | 100 | 100 | 100 | 100 | 100 | 100 | 100 |
| 6-5 | 63 | 70 | 65 | 50 | 75 | 60 | 60 | 70 | 30 | 80 | 0 |
| | 250 | 100 | 100 | 65 | 100 | 95 | 80 | 100 | 55 | 95 | 90 |
| 6-8 | 63 | 99 | 50 | 50 | 100 | 80 | 70 | 35 | 50 | 60 | 65 |
| | 250 | 100 | 100 | 60 | 100 | 100 | 70 | 100 | 75 | 85 | 95 |
| 6-15 | 63 | 90 | 80 | 70 | 75 | 90 | 80 | 70 | 55 | 50 | 0 |
| | 250 | 90 | 98 | 75 | 100 | 90 | 80 | 75 | 60 | 65 | 15 |

| Cmpd. no. | Rate g ai/ha | DIGSA | SOY | CORN | RICE | WHEAT |
|---|---|---|---|---|---|---|
| 1-4 | 63 | 35 | 10 | 65 | 10 | 15 |
| | 250 | 55 | 25 | 99 | 65 | 45 |

TABLE 13-continued

Herbicidal Activity of compounds in Table 12 when applied POST emergent at 63 and 250 ga.i./ha.

|     |     |     |     |     |     |     |
| --- | --- | --- | --- | --- | --- | --- |
| 1-9 | 63  | 70  | 55  | 75  | 45  | 50  |
|     | 250 | 95  | 75  | 100 | 50  | 80  |
| 1-11 | 63  | 40  | 15  | 35  | 65  | 30  |
|     | 250 | 55  | 15  | 95  | 65  | 45  |
| 1-14 | 63  | 0   | 0   | 0   | 0   | 0   |
|     | 250 | 0   | 0   | 50  | 0   | 0   |
| 1-15 | 63  | 10  | 0   | 40  | 0   | 0   |
|     | 250 | 10  | 5   | 60  | 30  | 15  |
| 1-16 | 63  | 30  | 100 | 100 | 45  | 70  |
|     | 250 | 98  | 100 | 100 | 98  | 100 |
| 1-23 | 63  | 75  | 99  | 80  | 45  | 60  |
|     | 250 | 75  | 100 | 100 | 85  | 99  |
| 1-24 | 63  | 20  | 8   | 90  | 60  | 15  |
|     | 250 | 35  | 15  | 95  | 65  | 60  |
| 1-29 | 63  | 85  | 0   | 10  | 0   | 0   |
|     | 250 | 100 | 20  | 50  | 10  | 15  |
| 4-4 | 63  | 98  | 15  | 25  | 10  | 8   |
|     | 250 | 100 | 65  | 90  | 55  | 70  |
| 4-8 | 63  | 0   | 10  | 90  | 0   | 10  |
|     | 250 | 75  | 40  | 100 | 15  | 50  |
| 4-9 | 63  | 50  | 10  | 0   | 0   | 0   |
|     | 250 | 99  | 30  | 50  | 0   | 0   |
| 5-2 | 63  | 50  | 55  | 95  | 8   | 10  |
|     | 250 | —   | —   | —   | —   | —   |
| 5-3 | 63  | 60  | 90  | 60  | 10  | 10  |
|     | 250 | —   | —   | —   | —   | —   |
| 5-4 | 63  | 75  | 10  | 60  | 10  | 35  |
|     | 250 | —   | —   | —   | —   | —   |
| 5-6 | 63  | 20  | 0   | 30  | 0   | 0   |
|     | 250 | 99  | 20  | 35  | 35  | 0   |
| 5-7 | 63  | 0   | 0   | 0   | 10  | 10  |
|     | 250 | 50  | 0   | 15  | 0   | 10  |
| 6-4 | 63  | 50  | 10  | 100 | 60  | 30  |
|     | 250 | 70  | 45  | 100 | 65  | 50  |
| 6-5 | 63  | 75  | 10  | 50  | 0   | 0   |
|     | 250 | 80  | 25  | 90  | 60  | 40  |
| 6-8 | 63  | 50  | 40  | 50  | 0   | 0   |
|     | 250 | 60  | 55  | 55  | 110 | 25  |
| 6-15 | 63  | 20  | 0   | 20  | 0   | 15  |
|     | 250 | 50  | 30  | 25  | 0   | 30  |

TABLE 14

Herbicidal Activity of compounds in Table 12 applied PRE emergent at 63 and 250 g a.i./ha.

| Cmpd. no. | Rate g ai/ha | AMARE | ABUTH | CASOB | IPOHE | CHEAL | AMBEL | XANST | SETVI | ECHCG | SORHA |
| --- | --- | --- | --- | --- | --- | --- | --- | --- | --- | --- | --- |
| 1-4 | 63 | 40 | 30 | 0 | 75 | 15 | 0 | 0 | 0 | 0 | 0 |
|     | 250 | 95 | 99 | 90 | 100 | 100 | 40 | 60 | 35 | 40 | 35 |
| 1-9 | 63 | 100 | 95 | 30 | 60 | 99 | 50 | 20 | 40 | 40 | 60 |
|     | 250 | 100 | 100 | 90 | 100 | 100 | 99 | 70 | 80 | 70 | 99 |
| 1-11 | 63 | 100 | 100 | 70 | 70 | 100 | 60 | 0 | 50 | 15 | 35 |
|     | 250 | 100 | 100 | 99 | 100 | 100 | 98 | 40 | 100 | 99 | 99 |
| 1-14 | 63 | 95 | 30 | 0 | 10 | 100 | 35 | 40 | 0 | 0 | 70 |
|     | 250 | 100 | 90 | 50 | 65 | 100 | 70 | 65 | 55 | 70 | 95 |
| 1-15 | 63 | 100 | 100 | 45 | 100 | 100 | 100 | 75 | 100 | 75 | 100 |
|     | 250 | 100 | 100 | 90 | 100 | 100 | 100 | 100 | 100 | 100 | 100 |
| 1-16 | 63 | 100 | 100 | 98 | 100 | 100 | 99 | 75 | 90 | 35 | 75 |
|     | 250 | 100 | 100 | 99 | 100 | 100 | 99 | 100 | 99 | 98 | 99 |
| 1-23 | 63 | 100 | 100 | 98 | 98 | 100 | 85 | 100 | 55 | 50 | 70 |
|     | 250 | 100 | 100 | 98 | 100 | 100 | 100 | 100 | 99 | 75 | 99 |
| 1-24 | 63 | 80 | 98 | 50 | 100 | 100 | 50 | 50 | 10 | 0 | 0 |
|     | 250 | 99 | 99 | 95 | 100 | 100 | 75 | 90 | 45 | 50 | 40 |
| 1-29 | 63 | 100 | 100 | 50 | 90 | 100 | 75 | 0 | 99 | 55 | 99 |
|     | 250 | 100 | 100 | 100 | 100 | 100 | 100 | 90 | 100 | 100 | 100 |
| 4-4 | 63 | 100 | 100 | 65 | 100 | 100 | 75 | 0 | 50 | 30 | 60 |
|     | 250 | 100 | 100 | 98 | 100 | 100 | 100 | 60 | 90 | 90 | 90 |
| 4-8 | 63 | 100 | 100 | 60 | 95 | 100 | 60 | 30 | 65 | 0 | 0 |
|     | 250 | 100 | 100 | 90 | 100 | 100 | 99 | 60 | 100 | 15 | 80 |
| 4-9 | 63 | 100 | 100 | 80 | 100 | 100 | 90 | 35 | 100 | 55 | 65 |
|     | 250 | 100 | 100 | 100 | 100 | 100 | 100 | 100 | 100 | 99 | 100 |
| 5-2 | 63 | 100 | 95 | 55 | 95 | 100 | 60 | 0 | 70 | 40 | 70 |

TABLE 14-continued

Herbicidal Activity of compounds in Table 12 applied PRE emergent at 63 and 250 g a.i./ha.

| | | | | | | | | | | | | |
|---|---|---|---|---|---|---|---|---|---|---|---|---|
| 5-3 | 250 | — | — | — | — | — | — | — | — | — | — | — |
| 5-3 | 63 | 100 | 100 | 70 | 80 | 100 | 60 | 30 | 55 | 30 | 90 | |
| | 250 | — | — | — | — | — | — | — | — | — | — | |
| 5-4 | 63 | 100 | 100 | 30 | 100 | 100 | 70 | 40 | 50 | 40 | 85 | |
| | 250 | — | — | — | — | — | — | — | — | — | — | |
| 5-6 | 63 | 100 | 75 | 40 | 35 | 100 | 35 | 0 | 95 | 40 | 25 | |
| | 250 | 100 | 95 | 98 | 70 | 100 | 99 | 10 | 100 | 90 | 100 | |
| 5-7 | 63 | 60 | 50 | 0 | 0 | 100 | 0 | 0 | 30 | 0 | 15 | |
| | 250 | 100 | 99 | 50 | 30 | 100 | 50 | 0 | 80 | 0 | 20 | |
| 6-4 | 63 | 100 | 100 | 98 | 100 | 100 | 100 | 98 | 100 | 98 | 99 | |
| | 250 | 100 | 100 | 100 | 100 | 100 | 100 | 100 | 100 | 100 | 100 | |
| 6-5 | 63 | 99 | 95 | 50 | 100 | 99 | 70 | 55 | 60 | 55 | 85 | |
| | 250 | 100 | 100 | 70 | 100 | 100 | 100 | 99 | 85 | 90 | 99 | |
| 6-8 | 63 | 100 | 99 | 20 | 60 | 100 | 0 | 0 | 55 | 30 | 55 | |
| | 250 | 100 | 99 | 70 | 100 | 100 | 99 | 70 | 99 | 85 | 100 | |
| 6-15 | 63 | 100 | 100 | 65 | 15 | 100 | 70 | 30 | 75 | 0 | 40 | |
| | 250 | 100 | 100 | 99 | 95 | 100 | 95 | 60 | 98 | 35 | 95 | |

| Cmpd. no. | Rate g ai/ha | DIGSA | SOY | CORN | RICE | WHEAT |
|---|---|---|---|---|---|---|
| 1-4 | 63 | 0 | 5 | 35 | 0 | 0 |
| | 250 | 60 | 65 | 75 | 8 | 45 |
| 1-9 | 63 | 50 | 0 | 10 | 0 | 0 |
| | 250 | 70 | 50 | 75 | 45 | 60 |
| 1-11 | 63 | 50 | 10 | 0 | 5 | 0 |
| | 250 | 100 | 20 | 50 | 55 | 30 |
| 1-14 | 63 | 55 | 0 | 0 | 0 | 0 |
| | 250 | 70 | 0 | 0 | 50 | 20 |
| 1-15 | 63 | 100 | 65 | 25 | 55 | 40 |
| | 250 | 100 | 100 | 100 | 70 | 65 |
| 1-16 | 63 | 30 | 100 | 100 | 45 | 70 |
| | 250 | 98 | 100 | 100 | 98 | 100 |
| 1-23 | 63 | 75 | 99 | 80 | 45 | 60 |
| | 250 | 75 | 100 | 100 | 85 | 99 |
| 1-24 | 63 | 0 | 50 | 0 | 5 | 20 |
| | 250 | 40 | 100 | 100 | 30 | 60 |
| 1-29 | 63 | 85 | 0 | 10 | 0 | 0 |
| | 250 | 100 | 20 | 50 | 10 | 15 |
| 4-4 | 63 | 98 | 15 | 25 | 10 | 8 |
| | 250 | 100 | 65 | 90 | 55 | 70 |
| 4-8 | 63 | 50 | 10 | 0 | 0 | 0 |
| | 250 | 99 | 30 | 50 | 0 | 0 |
| 4-9 | 63 | 99 | 25 | 30 | 10 | 0 |
| | 250 | 100 | 100 | 95 | 15 | 10 |
| 5-2 | 63 | 60 | 30 | 0 | 50 | 0 |
| | 250 | — | — | — | — | — |
| 5-3 | 63 | 60 | 12 | 50 | 30 | 35 |
| | 250 | — | — | — | — | — |
| 5-4 | 63 | 55 | 12 | 10 | 55 | 35 |
| | 250 | — | — | — | — | — |
| 5-6 | 63 | 20 | 0 | 30 | 0 | 0 |
| | 250 | 99 | 20 | 35 | 35 | 0 |
| 5-7 | 63 | 0 | 0 | 0 | 0 | 0 |
| | 250 | 50 | 0 | 10 | 0 | 0 |
| 6-4 | 63 | 100 | 55 | 99 | 30 | 0 |
| | 250 | 100 | 99 | 100 | 60 | 85 |
| 6-5 | 63 | 90 | 35 | 15 | 55 | 30 |
| | 250 | 99 | 10 | 90 | 95 | 90 |
| 6-8 | 63 | 60 | 0 | 0 | 0 | 0 |
| | 250 | 95 | 15 | 45 | 60 | 55 |
| 6-15 | 63 | 85 | 0 | 0 | 0 | 0 |
| | 250 | 99 | 0 | 0 | 0 | 0 |

What we claimed is:

1. A compound represented by the formula (I) or its salt:

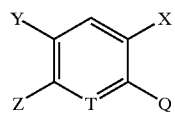

I wherein

X is hydrogen or halogen;

Y is represented by hydrogen, halogen, nitro, $(C_{1-4})$alkyl, $(C_{1-4})$alkoxy, $(C_{1-4})$haloalkyl or $(C_{1-4})$haloalkoxy;

T is represented by CII;

Z is the following group II;

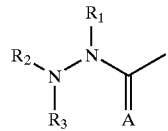

A is oxygen, sulfur or NR$_4$;

R$_1$, R$_2$, R$_3$ and R$_4$ are independent of each other and may be selected from the group consisting of hydrogen, cyano, (C$_{1-6}$)alkyl, (C$_{1-6}$)haloalkyl, (C$_{1-6}$)alkoxy, (C$_{1-6}$)haloalkoxy, (C$_{1-6}$)alkoxyalkyl, (C$_{2-6}$)alkynyl, (C$_{2-6}$)alkenyl, aryl, heteroaryl, aryloxy, heteroaryloxy, (C$_{3-6}$)cycloalkyl, (C$_{3-6}$)cyclocarbonyl, carboxy, (C$_{1-6}$)alkylcarbonyl, arylcarbonyl, (C$_{1-3}$)haloalkylcarbonyl, (C$_{1-6}$)alkylcarbonyloxy, (C$_{1-6}$)haloalkylcarbonyloxy, (C$_{1-6}$)alkoxycarbonyl, (C$_{1-6}$)haloalkoxycarbonyl, (C$_{1-6}$)alkylthiocarbonyl, (C$_{1-4}$)haloalkylthiocarbonyl, (C$_{1-6}$)alkoxythiocarbonyl, (C$_{1-6}$)haloalkoxythiocarbonyl, (C$_{1-4}$)alkylamino, arylsulfonylamino, arylamino, (C$_{1-6}$)alkylthio, arylthio, (C$_{2-6}$)alkenylthio, (C$_{2-6}$)alkynylthio, (C$_{1-6}$)alkylsulfinyl, (C$_{2-6}$)alkenylsulfinyl, (C$_{2-6}$)alkynylsulfinyl, (C$_{1-6}$)alkylsulfonyl, (C$_{2-6}$)alkenylsulfonyl, (C$_{2-6}$)alkynylsulfonyl, arylsulfonyl, where any of these groups may be optionally substituted with one or one more of the following group consisting of halogen, hydroxy, mercapto, cyano, nitro, amino, caboxy, (C$_{1-6}$)alkyl, (C$_{1-6}$)haloalkyl, (C$_{1-6}$)alkylcarbonyl, (C$_{1-6}$)alkylcarbonyloxy, (C$_{1-6}$)haloalkylcarbonyl, (C$_{1-6}$)haloalkylcarbonyloxy, (C$_{1-6}$)alkoxy, (C$_{1-6}$)alkoxycarbonyl, aminocarbonyl, (C$_{1-6}$)alkylaminocarbonyl, (C$_{1-6}$)haloalkoxy, (C$_{1-6}$)haloalkoxycarbonyl, (C$_{1-6}$)alkylsulfonyl, (C$_{1-6}$)haloalkylsulfonyl, aryl, haloaryl, alkoxyaryl, aryoxy, arylthio, haloalyloxy, heteroaryl, heteroaryloxy and (C$_{3-7}$)cycloalkyl;

when R$_2$ and R$_3$ are taken together with the atoms to which they are attached, they represent a three to seven membered substituted or unsubstituted ring optionally containing oxygen, carbonyl, S(O)$_{n^{**}}$ or nitrogen with following optional substitutions, one to three halogen, cyano, nitro, hydroxy, amino, carbonyl, (C$_{1-6}$)alkyl, (C$_{1-6}$)haloalkyl, (C$_{1-6}$)alkylcarbonyl, (C$_{1-6}$)alkylcarbonyloxy, (C$_{1-6}$)haloalkylcarbonyl, (C$_{1-6}$)haloalkylcarbonyloxy, (C$_{1-6}$)alkoxy, (C$_{1-6}$)alkoxycarbonyl, aminocarbonyl, (C$_{1-6}$)alkylaminocarbonyl, (C$_{1-4}$)haloalkoxy, (C$_{1-6}$)haloalkoxycarbonyl, (C$_{1-6}$)alkylsulfonyl, (C$_{1-6}$)haloalkylsulfonyl, aryl, heteroaryl or (C$_{3-7}$)cycloalkyl;

Q is selected from Q$_1$ or Q$_5$;
wherein

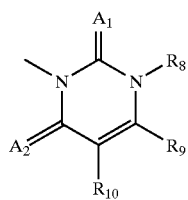

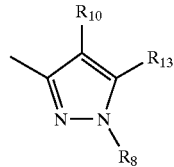

A$_1$ and A$_2$ are independently oxygen or sulfur;

R$_8$ is hydrogen, halogen, cyano, nitro, formyl, (C$_{1-4}$)alkyl, (C$_{1-4}$)haloalkyl, amino, (C$_{1-4}$)alkylamino, (C$_{1-4}$)haloalkylamino, (C$_{1-4}$)alkoxyamino, (C$_{1-4}$)haloalkoxyamino, (C$_{1-4}$)alkylcarbonyl, (C$_{1-4}$)haloalkylcarbonyl, (C$_{1-4}$) haloalkoxycarbonyl, (C$_{1-4}$)alkylcabonylamino, (C$_{1-4}$)haloalkylcarbonylamino, (C$_{1-4}$)alkoxycarbonylamino, (C$_{1-4}$)haloalkoxycarbonylamino, (C$_{1-6}$)alkoxyalkyl, (C$_{1-6}$)haloalkoxyalkyl, (C$_{1-6}$)alkylthio, (C$_{1-6}$)haloalkylthio, (C$_{2-6}$)alkenyl, (C$_{2-6}$)haloalkenyl, (C$_{2-6}$)alkynyl or (C$_{2-6}$)haloalkynyl; R$_9$ and R$_{10}$ are independent of each other and maybe selected from the group consisting of hydrogen, halogen, cyano, (C$_{1-4}$)alkyl, (C$_{1-4}$)haloalkyl, (C$_{1-4}$)alkoxy, (C$_{1-4}$)haloalkoxy, (C$_{2-6}$)alkenyl, and (C$_{2-6}$)haloalkenyl, R$_{13}$ may be selected from the group consisting of hydrogen, halogen, cyano, (C$_{1-4}$alkyl, (C$_{1-4}$)alkoxy, (C$_{1-4}$)haloalkoxy, (C$_{1-4}$)alkylthio, (C$_{1-4}$)haloalkylthio, (C$_{1-4}$)alkylsulfinyl, (C$_{1-4}$)haloalkylsulfinyl, (C$_{1-4}$)alkylsulfonyl, (C$_{1-4}$)haloalkylsulfonyl, (C$_{2-6}$)alkenyl, and (C$_{2-6}$)haloalkenyl;

n$^{**}$ is represent an integer from 0 to 2.

2. A compound or its salt according to the claim 1 wherein

X is hydrogen or halogen;

Y is represented by hydrogen, halogen, nitro, (C$_{1-4}$)haloalkyl or (C$_{1-4}$)haloalkoxy;

T is CH;

A is oxygen or sulfur;

R$_1$, R$_2$, and R$_3$ are independent of each other and may be selected from the group consisting of hydrogen, (C$_{1-6}$)alkyl, (C$_{1-4}$)haloalkyl, (C$_{1-6}$)alkoxy, (C$_{1-6}$)haloalkoxy, (C$_{1-6}$)alkoxyalkyl, (C$_{2-6}$)alkynyl, (C2$_6$)alkenyl, aryl, heteroaryl, aryloxy, heteroaryloxy, (C$_{3-6}$)cycloalkyl, (C$_{3-4}$)cyclocarbonyl, carboxy, (C$_{1-6}$)alkylcarbonyl, arylcarbonyl, (C$_{1-6}$)alkoxycarbonyl, (C$_{1-6}$)haloalkoxycarbonyl, (C$_{1-6}$)alkylthiocarbonyl, (C$_{1-6}$)alkoxythiocarbonyl, (C$_{1-6}$)alkylamino, arylsulfonylamino, arylamino, (C$_{1-6}$)alkylthio, arylthio, (C$_{2-6}$)alkenylthio, (C$_{1-6}$)alkylsulfinyl, (C$_{2-4}$alkenylsulfinyl, (C$_{2-6}$)alkynylsulfinyl, (C$_{1-6}$)alkylsulfonyl, (C$_{2-4}$)alkenylsulfonyl, arylsulfonyl, where any of these groups maybe optionally substituted with one or one more of the following group consisting of halogen, hydroxy, mercapto, cyano, nitro, amino, caboxy, (C$_{1-6}$)alkyl, (C$_{1-4}$)haloalkyl, (C$_{1-6}$)alkylcarbonyl, (C$_{1-6}$)alkylcarbonyloxy, (C$_{1-6}$)haloalkylcarbonyl, (C$_{1-6}$)haloalkylcarbonyloxy, (C$_{1-6}$)alkoxy, (C$_{1-6}$)alkoxycarbonyl, aminocarbonyl, (C$_{1-6}$)alkylaminocarbonyl, (C$_{1-6}$)haloalkoxy, (C$_{1-6}$)haloalkoxycarbonyl, (C$_{1-4}$)alkylsulfonyl, (C$_{1-6}$)haloalkylsulfonyl, aryl, haloaryl, alkoxyaryl, aryoxy, arylthio, haloaryloxy, heteroaryl, heteroaryloxy and (C$_{3-7}$)cycloalkyl;

Q is selected from Q$_1$, or Q$_5$; wherein

A$_1$ and A$_2$ are independently oxygen or sulfur;

$R_8$ is hydrogen, $(C_{1-4})$alkyl, $(C_{1-4})$haloalkyl, or amino;

$R_9$ and $R_{10}$ are independent of each other and may be selected from the group consisting of hydrogen, halogen, cyano, $(C_{1-4})$alkyl, $(C_{1-4})$haloalkyl, $(C_{1-4})$alkoxy, $(C_{1-4})$haloalkoxy, $(C_{2-6})$alkenyl, and $(C_{2-6})$haloalkenyl;

$R_{13}$ may be selected from the group consisting of hydrogen, halogen, $(C_{1-4})$alkyl, $(C_{1-4})$alkoxy, $(C_{1-4})$haloalkoxy, $(C_{1-4})$alkylthio, $(C_{1-4})$haloalkylthio, $(C_{1-4})$alkylsulfinyl, $(C_{1-4})$haloalkylsulfinyl, $(C_{1-4})$alkylsulfonyl or $(C_{1-4})$haloalkylsulfonyl.

3. A compound or its salt according to the claim 2 wherein

X and Y are independent of each other represent hydrogen or halogen;

T is CH;

Z is selected from group (II);

A is oxygen;

$R_1$, $R_2$ and $R_3$ are independent of each other and may be selected from the group consisting of hydrogen, $(C_{1-6})$alkyl, $(C_{1-6})$haloalkyl, $(C_{1-6})$alkoxy, $(C_{1-6})$haloalkoxy, $(C_{1-6})$alkoxyalkyl, $(C_{2-4})$alkynyl, $(C_{2-4})$alkenyl, aryl, heteroaryl, aryloxy, heteroaryloxy, $(C_{3-6})$cycloalkyl, $(C_{3-6})$cyclocarbonyl, carboxy, $(C_{1-6})$alkylcarbonyl, arylcarbonyl, $(C_{1-3}, (C_{1-6}))$alkoxycarbonyl, $(C_{1-6})$haloalkoxycarbonyl, $(C_{1-6})$alkylthiocarbonyl, $(C_{1-6})$alkoxythiocarbonyl, $(C_{1-6})$alkylamino, arylsulfonylamino, arylamino, $(C_{1-4})$alkylthio, arylthio, $(C_{2-6})$alkenylthio, $(C_{1-6})$alkylsulfinyl, $(C_{2-6})$alkenylsulfinyl, $(C_{2-6})$alkynylsulfinyl, $(C_{1-6}))$alkylsulfonyl, $(C_{2-6}))$alkenylsulfonyl, and arylsulfonyl, Q is selected from $Q_1$, or $Q_5$;

wherein $A_1$ and $A_2$ are oxygen;

$R_5$ is $(C_{1-4})$alkyl, $(C_{1-4})$haloalkyl, amino;

$R_9$ and $R_{10}$ are independent of each other and may be selected from the group consisting of hydrogen, $(C_{1-4})$alkyl, $(C_{1-4})$haloalkyl, $(C_{1-4})$alkoxy, $(C_{1-4})$haloalkoxy, $(C_{2-6})$alkenyl, $(C_{2-6})$haloalkenyl;

$R_{13}$ may be selected from the group consisting of hydrogen, halogen, cyano, $(C_{1-4})$alkoxy, $(C_{1-4})$haloalkoxy, and hydroxy.

4. A herbicidal composition, characterized in that it contains at least one compound according to claim 1.

5. A herbicidal composition which comprises an effective amount of a compound or its salt of claim 1 and an agricultural adjuvant.

6. The herbicidal composition according to claim 5 wherein the compounds are formulated into a practical use form selected from the group consisting of emulsifiable concentrate (EC), aqueous and oil based suspension concentrate (SC), wettable powder (WP), water dispersible granule (WDG) or microenscapulated (ME) form.

7. A method for controlling the growth of undesired plant species in plantation crops which comprises applying to the locus of the crop a herbicidally effective amount of a compound or its salt according to claim 1.

8. A method for controlling undesired vegetation in a crop field selected from the group consisting of corn, peanut, cotton, wheat, sorghum, sunflower, soybean and rice by applying to the locus of the crop to be protected a herbicidally effective amount of a compound or its salt of claim 1.

9. A method for controlling weeds, which comprises applying to the locus to be protected a herbicidally effective amount of a compound or its salt of claim 1 in combination with one or more other herbicides for providing an additive or synergistic herbicidal effect.

10. A method for controlling weeds of claim 7 wherein the compound or its salt is applied to the soil as a pre-plant incorporated, pre-emergent or delayed pre-emergent herbicide.

11. A method for controlling weeds of claim 9 wherein the compound or its salt is applied to the soil as a pre-plant incorporated, pre-emergent or delayed pre-emergent herbicide.

12. A method for controlling weeds of claim 7 wherein the compound or its salt is applied as a post-emergent herbicide to plant foliage.

13. A method for controlling weeds of claim 9 wherein the compound or its salt is applied as a post-emergent herbicide to plant foliage.

14. A method for controlling weeds of claim 9 wherein the other herbicide is an acetanilide, oxyacetamide, sulfonylurea, triazine, triketone, urea, amide or glyphosate.

15. A method to defoliate potato and cotton using a compound or its salt of claim 1.

* * * * *